United States Patent [19]

Ward et al.

[11] Patent Number: 5,428,123
[45] Date of Patent: Jun. 27, 1995

[54] COPOLYMERS AND NON-POROUS, SEMI-PERMEABLE MEMBRANE THEREOF AND ITS USE FOR PERMEATING MOLECULES OF PREDETERMINED MOLECULAR WEIGHT RANGE

[75] Inventors: Robert S. Ward, Lafayette; Kathleen A. White, Pleasant Hill, both of Calif.

[73] Assignee: The Polymer Technology Group, Emeryville, Calif.

[21] Appl. No.: 52,361

[22] Filed: Apr. 23, 1993

Related U.S. Application Data

[63] Continuation-in-part of Ser. No. 874,336, Apr. 24, 1992, abandoned.

[51] Int. Cl.$^6$ .................................................. C08G 77/04
[52] U.S. Cl. .................................. 128/28; 528/25; 528/10; 528/34; 210/100.21; 210/500.23; 525/453; 525/459; 525/460
[58] Field of Search ................. 128/28, 25, 80, 34; 525/453, 459, 460; 210/500.21, 500.23

[56] References Cited

U.S. PATENT DOCUMENTS

| | | | |
|---|---|---|---|
| 3,804,786 | 4/1974 | Sekmakas | 260/18 |
| 3,826,768 | 7/1974 | Suzuki et al. | 260/29.2 |
| 3,852,090 | 12/1974 | Leonard et al. | 117/14 |
| 4,124,572 | 11/1978 | Mao | 528/76 |
| 4,183,836 | 1/1980 | Wolfe, Jr. | 260/29.2 |
| 4,190,566 | 2/1980 | Noll | 260/29.2 |
| 4,202,880 | 5/1980 | Fildes et al. | 424/78 |
| 4,202,957 | 5/1980 | Bunk et al. | 528/77 |
| 4,224,432 | 9/1980 | Pechhold et al. | 528/76 |
| 4,367,327 | 1/1983 | Holker et al. | 528/61 |
| 4,743,629 | 5/1988 | Karakelle et al. | 521/175 |
| 4,849,458 | 7/1989 | Reed et al. | 521/159 |
| 4,892,538 | 1/1990 | Aebischer et al. | 424/424 |
| 5,017,664 | 5/1991 | Grasel et al. | 525/454 |
| 5,047,456 | 9/1991 | Onwumere et al. | 524/13 |
| 5,079,168 | 1/1992 | Amiot | 437/284 |

FOREIGN PATENT DOCUMENTS

| | | |
|---|---|---|
| 0069852A1 | 5/1982 | European Pat. Off. |
| 0107915A1 | 5/1984 | European Pat. Off. |
| 107915 | 5/1984 | European Pat. Off. |
| 0333899A2 | 3/1988 | European Pat. Off. |
| 0272682 | 6/1988 | European Pat. Off. |
| 2049544 | 12/1980 | United Kingdom |
| 2073219 | 10/1981 | United Kingdom |
| WO85/05322 | 12/1985 | WIPO |
| WO85/05373 | 12/1985 | WIPO |

OTHER PUBLICATIONS

Text Book of Polymer Science, Billmeyer, Jr., 1962, pp. 6, 7, 13, 53 and 54.

(List continued on next page.)

*Primary Examiner*—Paul R. Michl
*Assistant Examiner*—Duc Truong
*Attorney, Agent, or Firm*—Pennie & Edmonds

[57] ABSTRACT

A biocompatible, hydrophilic, segmented block polyurethane copolymer which comprises 5 to 45 wt % of a hard segment and 95 to 55 wt % of a soft segment selected from a hydrophilic, hydrophobic and amphipathic oligomer is disclosed. The copolymer is capable of forming a non-porous, semi-permeable film of a tensile strength greater than 300 and up to 10,000 psi, and has an ultimate elongation greater than 300% and up to 1,500% and a water absorption such that the sum of the volume fraction of absorbed water and the hydrophilic volume fraction of the soft segment exceeds about 100% and is up to about 2,000% of the dry polymer volume. The film is permeable to cell nutrients and waste molecules of up to about 6,000 to 600,000 molecular weight and is substantially impermeable to cells and particulate matter. A non-porous, semi-permeable, biocompatible film is formed from the block copolymer of the invention in the form of a flexible sheet or a hollow fiber. Also disclosed is a method of permeating molecules of a predetermined molecular weight range while preventing the passage of larger molecular weight molecules, cells, and condensed phases of matter between two fluids comprising interposing between the two fluids the non-porous film of the invention.

57 Claims, 3 Drawing Sheets

OTHER PUBLICATIONS

A. B. Trezvova, et al., "Study of Semipermeable Membranes," Chemical Abstracts, 106:398 (1987).

Paynter, et al., "The Hydrolytic Stability of Mitrathane, a Polyuretheneurea-An X-ray Photoelectron Spectroscopy Study", *J. Biomed Mater. Res.* 22:687–698 (1988).

Szycher, et al. "Blood Compatible Polyurethane Elastomers", *J. Biomater. Appl.* 2:290–313 (1987).

Okkema et al., "Bulk Surface, and Blood-Contacting Properties of Polyurethanes Modified with Polyethylene Oxide", *J. Biomater Sc. Polymer.* Edn.1(1):43–62 (1989).

Takahara, et al., "Surface Molecular Mobility and Platelet Reactivity of (SPUUS) with Hydrophilic and Hydrophobic Soft Segment Components":, *J. Biomater. Sci. Polymer.* Edn. 1(1):7–29 (1989).

Chen, et al., "Synthesis, Characterization and Permeation Properties of Polyether Based Polyurethanes", *J. Appl. Polym. Sci.* 16: 2105–2114 (1972).

COPOLYMERS AND NON-POROUS, SEMI-PERMEABLE MEMBRANE THEREOF AND ITS USE FOR PERMEATING MOLECULES OF PREDETERMINED MOLECULAR WEIGHT RANGE

This application is a CIP of Ser. No. 07/874,336, now abandoned filed Apr. 24, 1992.

BACKGROUND OF THE INVENTION

1. Field of the Invention

This invention relates to a biocompatible, hydrophilic, segmented block copolymer that comprises hard and soft segments in a predefined proportion. The copolymers have hydrophilic or amphipathic soft segments that provide permeability to films and membranes prepared therefrom due to their lyophilicity, hydrophilicity and molecular weight, and hard segments that provide high cohesive energy reinforcement. The polymers of the invention may be cast into flexible sheets and/or hollow membrane shapes. The copolymers of this invention form strong, optically-clear, dense membranes which are selectively permeable to gases, ions, proteins and other macromolecules. The molecular weight cut-off of the membrane is controlled by varying the soft segment content, soft segment polarity/hydrophilicity and soft segment molecular weight.

2. Description of the Background

In general, polyetherurethane block or segmented copolymers exhibit good biocompatibility along with high strength and elastomeric properties. This unique combination of properties is due in part to the two-phase morphology of the polyurethane molecule. In a typical polyurethane, aggregated aromatic or aliphatic urethane or urea segments constitute a hard glassy or semicrystalline phase, while low glass transition temperature (Tg) oligomeric segments comprise the liquid-like, rubbery soft phase or segment. The morphology of a polyurethane depends on many factors, including hard and soft segment chemistry, segment polarity differences, hard segment content, and hard and soft segment molecular weights.

In both polyurethaneureas and polyurethanes, the chemistry of the soft segment affects the degree of phase separation in the polymer, which in turn affects its bulk and surface properties and subsequent biocompatibility. Polyurethaneureas, similar to the ones disclosed in this patent only as to their hard segment compositions, have been shown to be resistant to degradation in several applications (Paynter, et al., "The Hydrolytic Stability of Mitrathane, a Polyurethaneurea—An X-ray Photoelectron Spectroscopy Study", J. Biomed. Mater. Res. 22:687–698 (1988); Szycher, et al. "Blood Compatible Polyurethane Elastomers", J. Biomater. Appl. 2:290–313 (1987)).

The application of natural and synthetic polymer membranes to the separation of gaseous and liquid mixtures of low molecular weight has been reported in a number of reviews. Many studies of membrane permeability to simple low molecular weight (MW) permeants have been reported in which the composition of glassy-rubbery or crystalline-rubbery copolymers are varied. A polyurethane multipolymer membrane different from the one disclosed herewith has been shown to be water and salt permeable. In thermoplastic segmented block copolymers where one block or segment is glassy or crystalline (hard segment) and another is rubbery or liquid-like (soft segment), the permeation of molecules occurs primarily through the soft segment. The relatively impermeable hard segment, provides physical integrity to the polymer by virtue of its strong intermolecular interactions with like segments on adjacent molecules, even under conditions which may cause swelling of the soft segment.

Okkema, et al. discloses a series of polyether polyurethanes based on polyethylene oxide (PEO), polytetramethylene oxide (PTMO) and mixed PEO/PTMO soft segments suitable as blood contacting surfaces, but with a hard segment content of 55 wt %, too high to be useful in the present invention. (Okkema et al., "Bulk Surface and Blood-Contacting Properties of Polyurethanes Modified with Polyethylene Oxide", J. Biomater. Sci. Polymer. Edn.1(1):43–62 (1989)).

Takahara, et al. discloses the preparation of Segmented Poly (etherurethaneureas) (SPUU) with hydrophilic and hydrophobic polyether components. (Takahara et al., "Surface Molecular Mobility and Platelet Reactivity of (SPUUS) with Hydrophilic and Hydrophobic Soft Segment Components", J. Biomater. Sci. Polymer. Edn. 1(1):17–29 (1989)). Platelet adhesion and dynamic contact angle measured after adsorption of bovine serum albumin revealed that the SPUUs with hydrophilic soft segments had a non-adhesive surface.

Chen, et al. examines the relationship between structure and properties of polyether based polyurethanes. (Chen et al., "Synthesis, Characterization and Permeation Properties of Polyether Based Polyurethanes", J. Appl. Polym. Sci. 16: 2105–2114 (1972)). Of particular interest is the testing of the transport of water and low molecular weight salt through polymeric membranes made of elastomers that are block copolymers consisting of hard and soft segments, with the former acting as physical crosslinks.

U.S. Pat. No. 3,804,786 to Sekmakas discloses water-dispersible cationic resins, particularly polyurethane resins prepared by reaction of a resinous polyepoxide with a polyisocyanate to provide an hydroxy-functional polyurethane with tertiary amine functionality. These resins are useful for electrode position at the cathode.

U.S. Pat. No. 3,826,768 to Suzuki and Osonol discloses a process for preparing polyurethane compositions by dispersion of polyurethane-containing isocyanates made from polyols and organic isocyanates in water under specified conditions.

U.S. Pat. No. 3,852,090 to Leonard et al. discloses the utilization of a urethane film for waterproofing a breathable textile substrate.

U.S. Pat. No. 4,124,572 to Mao relates to thermoplastic polyurethanes prepared by a specified method. The thus produced elastomers are useful for automotive products, applications such as cattle ear tags, coatings and coated fabrics.

U.S. Pat. No. 4,183,836 to Wolfe, Jr. discloses a water-based polyurethane dispersion and its preparation by reacting an aliphatic diisocyanate with three critical active hydrogen compounds to form a pre-polymer containing carboxyl and free isocyanate groups, and then dispersing the pre-polymer in an aqueous medium with a tertiary amine and a diamine. These dispersions are useful in coating applications such as textile materials.

U.S. Pat. No. 4,190,566 to Noll et al. relates to non-ionic, water dispersible polyurethanes with substantially linear molecular structure and lateral polyalkylene oxide polyether chains containing ethylene oxide units of specified content.

U.S. Pat. No. 4,202,880 to Fildes et al., discloses sustained release delivery means comprising a biologically active agent, i.e., a drug, a linear hydrophilic block polyoxyalkylene-polyurethane copolymer, and optionally a buffer. A single hydrophilic soft segment is used. Only the hard segment is hydrophobic.

U.S. Pat. No. 4,202,957 to Bunk, et al. discloses polyurethane polyether-based elastomers which are thermoplastic and recyclable, and have increased high temperature resistance that makes them suitable for injection molding.

U.S. Pat. No. 4,224,432 to Pechhold et al. discloses a polyurethane comprising a reaction product of a polymerizate of tetrahydrofuran and an alkylene oxide, an organic polyisocyanate and a chain extender which is an aliphatic polyol or a polyamine. 2001.

U.S. Pat. No. 4,367,327 to Holker et al. relates to a breathable polyurethane film for coating fabrics to make them waterproof. The polyurethane film comprises in stoichiometric amounts a hard segment made of a low molecular weight diisocyanate with a difunctional compound, and a soft segment comprising polyethylene glycol. The mechanical properties of the film are improved by crosslinking with a triisocyanate.

U.S. Pat. No. 4,849,458 to Reed et al. discloses a hydrophilic, segmented polyether polyurethane-urea exhibiting increased tensile strength and elongation when wet with water. The polymers form clear films that are permeable to water vapor.

Many of these materials are segmented polyurethane elastomers. Some of them, moreover, have found biomedical applications virtually without being modified. However, despite their widespread use, many biomaterials were originally developed for nonmedical uses. In fact, most polyurethane materials were developed to satisfy high volume, industrial needs. A most notable example is DuPont's LYCRA ® Spandex, a polyurethane utilized in the fabrication of circulatory support device components. This material was later sold under the trade name BIOMER ® Segmented Polyurethane.

AVCOTHANE-51 ® resulted from the combination of two commercially available polymers, a silicone and a polyurethane, both of which are widely used as fabric coatings. AVCOTHANE-51 ® is utilized in biomedical devices such as an intra-aortic balloon. The sole improvements introduced for its biomedical applications were the use of highly purified starting materials, the filtration of the product solution and clean conditions for the fabrication of blood-contacting surfaces. Another biomedical polyurethane, AVCOTHANE-610 ®, also called CARDIOMAT-610 ®, and ANGIOFLEX ® are presently being used in blood pumps and trileaflet heart valves.

The thermoplastic material PELLETHANE ® was first applied to the manufacture of cannulae for blood vessels, and later of catheters. This material had originally been developed as an extrusion molding resin exhibiting superior hydrolytic stability than their polyester-based counterparts. Table 1 below lists some of the biomedical polyurethanes available in the U.S. market.

The known materials listed in Table 1 below may be essentially divided into two groups, where for each group one material is derived from the previous one, and so on.

TABLE 1

| Biomedical Polyurethanes |
| --- |
| AVCOTHANE-51/CARDIOTHANE-51 (10% silicone) |
| AVCOTHANE-610/CARDIOTHANE-610/ANGIOFLEX |
| Biothane |
| BIOMER/LYCRA Spandex/Mitrathane |
| BPS-215 |
| Estane 5714 |
| Extrudable BIOMER |
| PELLETHANE 2363/Renathane |
| Superthane |
| Tecoflex |
| Texin |
| Tygothane |
| Vialon |

If the polyesterurethanes, which exhibit low hydrolytic stability, are eliminated from the list, two classes of polyetherurethanes remain. These are the polyurethanes containing solely urethane groups, and polyurethaneureas, which also contain urea groups. Table 2 below lists some of the common reactants used in polyurethane synthesis.

TABLE 2

| Reactants of Biomedical Polyurethanes |
| --- |
| POLYETHER |
| $H(O-CH_2-CH_2-CH_2-CH_2-)_nOH$ |
| polytetramethylene oxide (PTMO) |
| polytetramethyleneetherglycol (PTMEG) |
| polytetrahydrofuran (poly(THF)) |
| DIISOCYANATE |
| $OCN-Ph-CH_2-Ph-NCO$ |
| 4,4-diphenylmethane diisocyanate (MDI) |
| CHAIN EXTENDERS |
| $HO-CH_2-CH_2-CH_2-CH_2-OH$ |
| Polyurethanes: Butane Diol (BD) |
| $H_2N-CH_2-CH_2-NH_2$ |
| Polyurethaneureas: Ethylene Diamine (ED) |

The majority of useful biomedical elastomers are those prepared from polyether glycols. A most commonly-used polyether glycol is a product of the ring-opening polymerization of tetrahydrofuran (THF). This polyether is known mostly as polytetramethyleneetherglycol (PTMEG), polytetramethyleneoxide (PTMO) and polytetrahydrofuran (poly(THF)). The present inventors have found that polyurethanes containing only soft segments of PTMO are impermeable to permeants as low as 180 daltons MW (glucose) and are, therefore, unsuitable for use in the present invention.

The most commonly used diisocyanate is 4,4-diphenylmethanediisocyanate (MDI). MDI-based polyurethane elastomers generally have physical and mechanical properties that are superior to polymers prepared from tolylene diisocyanate (TDI), or the aliphatic diisocyanates such as hexamethylene diisocyanate (HDI) and dicyclohexanediisocyanate (HMDI), a hydrogenated MDI analogue. Aliphatic diisocyanates produce non-yellowing polymers upon exposure to ultraviolet radiation and are thus extremely desirable for industrial and apparel coating applications. HMDI hard segments are often too miscible with the polyether segments to provide the degree of phase separation required to achieve optimal mechanical properties. This is particularly true at elevated temperatures, such as 37° C., which significantly decrease the physical strength of a polymer. Phase separation is, therefore, important for attaining good physical properties in polyurethane elastomers. This relationship is discussed further below.

The reaction of isocyanate groups with low molecular weight difunctional reagents leads to chain extension, and to the formation of hard segments connecting the polyether soft segments through urethane groups. If the chain extender is a diol, the hard segment has repeat units connected by urethane groups, whereas if it is a diamine, the hard segment comprises urea groups. In the later case, the resulting polymer is referred to as a polyurethaneurea, although in common useage, both groups are often referred to as polyurethanes. Some of the properties of these elastomers are shown in Table 3 below.

TABLE 3

| Biomedical Polyurethane Properties | |
|---|---|
| POLYURETHANES e.g, PELLETHANE 2363[1] | POLYURETHANEUREAS e.g., BIOMER[2] |
| moderate phase separation | good phase separation |
| thermoplastic | solvent cast (unless H$_2$O extended) |
| >70A shore hardness | low hardness/modulus possible |
| moderate toughness | extreme toughness |
| moderate hysteresis/creep | low hysteresis/creep |
| good flex fife | excellent flex life |
| severe distortion in autoclave | autoclavable |

[1]MDI/PTMO/BD
[2]MDI/PTMO/ED

The chemical composition of the permeable, rubbery phase of a block copolymer may be varied in this invention without resulting in a significant variation in its total volume fraction or glass transition temperature. Polyurethanes like the PELLETHANE 2363 ® series are moderately phase-separated thermoplastics generally having a shore hardness of 70A or higher. These polymers are reasonably tough and resistant to fatigue, but exhibit a high level of hysteresis or creep under load. These polyurethanes are usually unable to withstand autoclaving without distortion and molecular weight reduction. Polyurethaneureas like BIOMER ® are more highly phase-separated elastomers which are generally manufactured in solution unless the diamine chain extender is completely replaced by water, as it is in the extrudable BIOMER ® polymer. When the total content of hard segment is lowered, useful urea-containing urethanes are obtained. These are elastomers approaching natural rubber characteristics. Both BIOMER ® and the polyether PELLETHANES ® have pure PTMO soft segments and are unsuitable for use in the present invention.

A combination of high elongation at break and high ultimate tensile strength make the polyurethaneureas tougher than the corresponding polyurethanes. Their low hysteresis or creep properties, however, are probably their most outstanding feature. Polyurethaneureas exhibit excellent flex life when subjected to biaxial strain, such as in a blood pump. Finally, polyurethaneureas can withstand one or two autoclave cycles without evidencing a significant decrease in molecular weight or physical properties. This is indicative of a superior ability to retain their properties at elevated temperatures relative to their polyurethane analogues.

Although many polyurethanes and polyurethaneureas are available commercially, some of which were discussed above, none forms membranes of permeability, strength, flexibility and biocompatiblity required for growing cells by permitting the passage of nutrients, cell products and cell waste materials while preventing the passage of immunological or microbiological substances that might be detrimental to cell growth and the manufacture of cell products.

SUMMARY OF THE INVENTION

This invention relates to a biocompatible, hydrophilic, segmented block polyurethane copolymer, comprising about 5–45 wt % of at least one hard segment;

about 95–55 wt % of at least one soft segment, comprising at least one hydrophilic, hydrophobic or amphipathic oligomer selected from the group consisting of aliphatic polyols, aliphatic or aromatic polyamines and mixtures thereof; the copolymer being capable of forming a substantially non-porous, semi-permeable film having a tensile strength greater than about 350 psi and up to about 10,000 psi, an ultimate elongation greater than about 300% and up to about 1,500% and a water absorption such that the sum of the hydrophilic volume fraction of the soft segment and the absorbed water volume fraction is greater than about 100% and up to about 2,000% of the dry polymer volume and greater than about 50% and up to about 95% of the wet polymer volume and being permeable to molecules of molecular weight up to about 6,000 to 600,000 daltons and substantially impermeable to cells and particulate matter.

This invention also relates to a non-porous, semi-permeable, biocompatible film formed from the block copolymer described above.

Also encompassed herein is a method of permeating molecules of a predetermined molecular weight range while substantially preventing the passage of cells and particulate matter between two fluids, the method comprising interposing between the two fluids a non-porous, semi-permeable, biocompatible film formed from the copolymer of the invention.

A more complete appreciation of the invention and many of the attendant advantages thereof will be readily perceived as the same becomes better understood by reference to the following brief description of the drawings.

Figure 1:
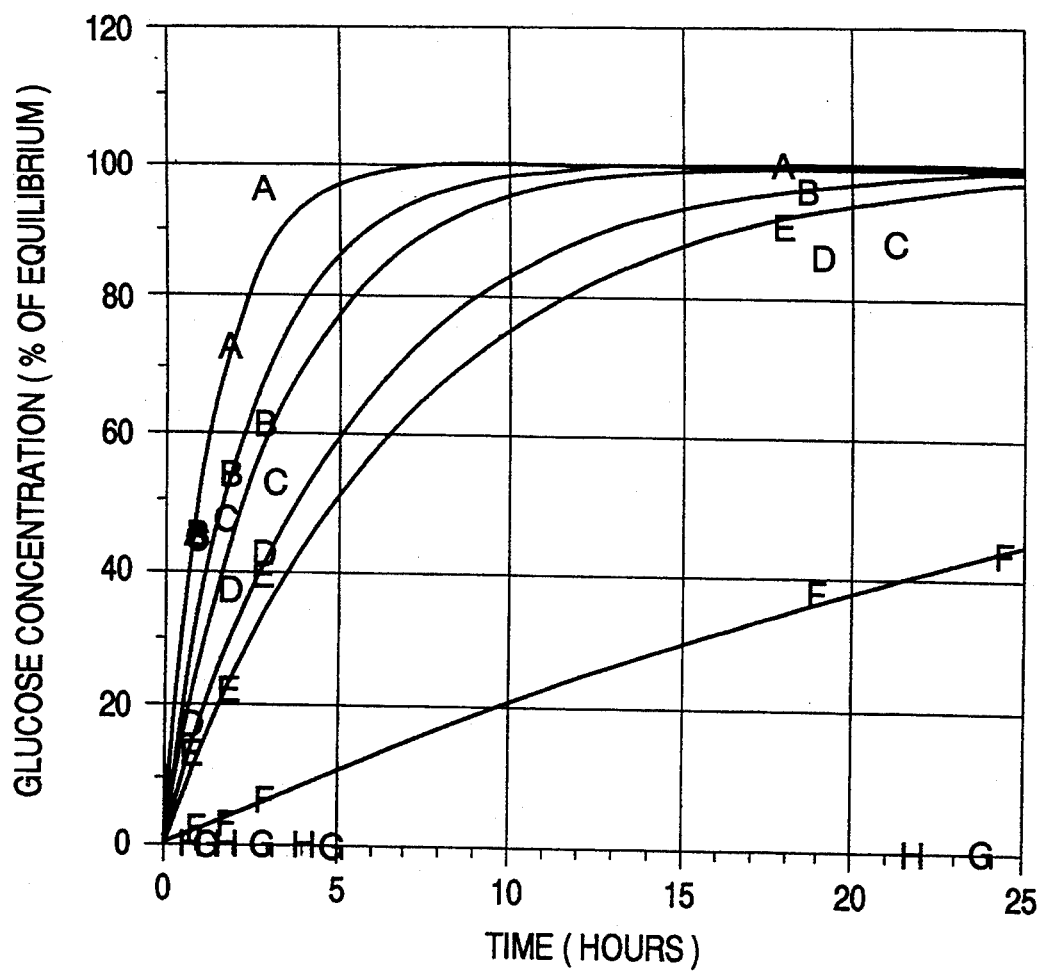
FIG. 1 depicts the variation in glucose permeability vs. time through dense membranes of the inventor with varying hydrophilicity. The wt % hydrophilic content or hydrophilicity is as follows: A (85%); B (66%); C (50%); D (40%); E (30%); F (20%); G (10%); H (0%).
Figure 2:
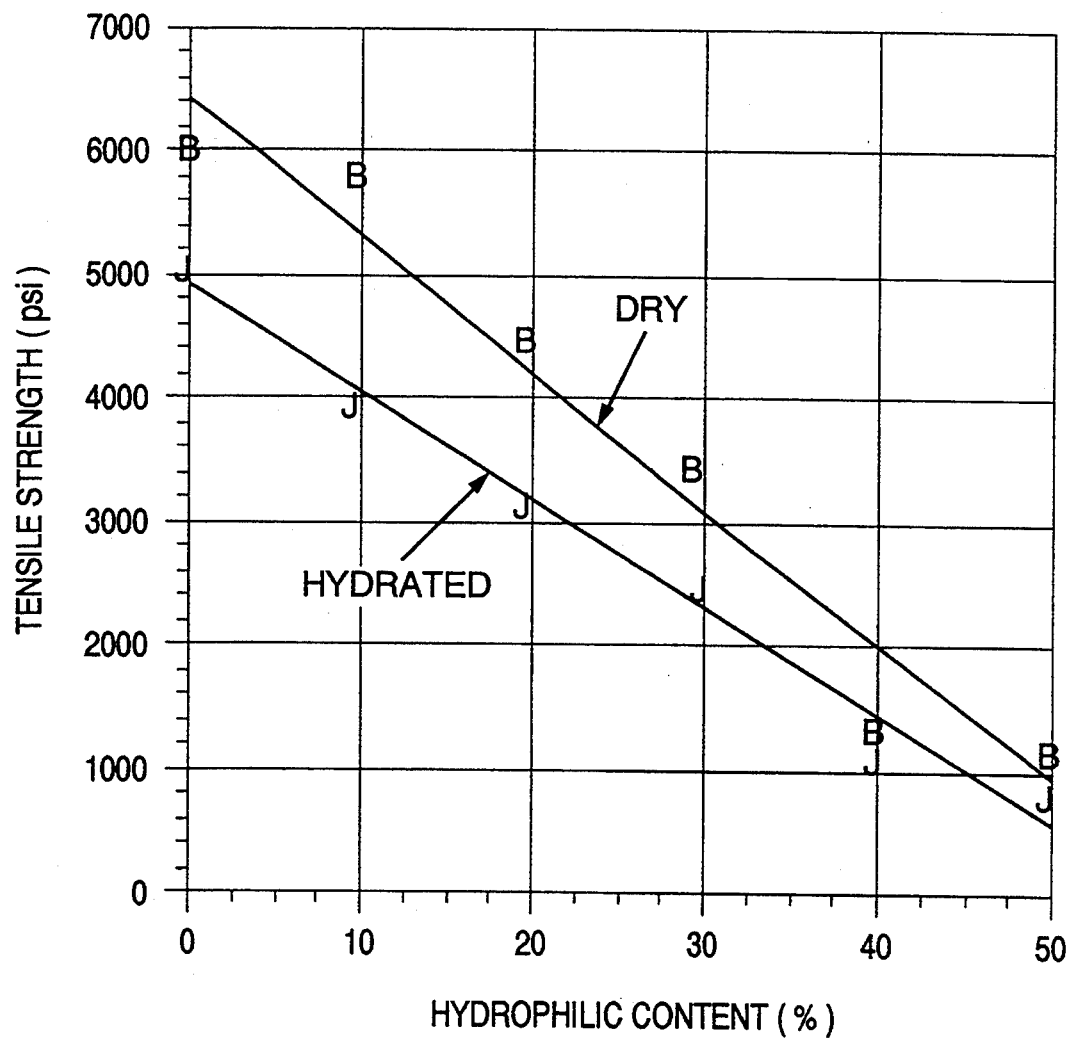
FIG. 2 shows the correlation of membrane tensile strength vs. hydrophilic content of the polymers of the present invention. In every case the tensile strength of the hydrated membrane is lower than that of the dry membrane. The difference is small, however, and useful polymers may be obtained even at high hydrophilic contents.
Figure 3:
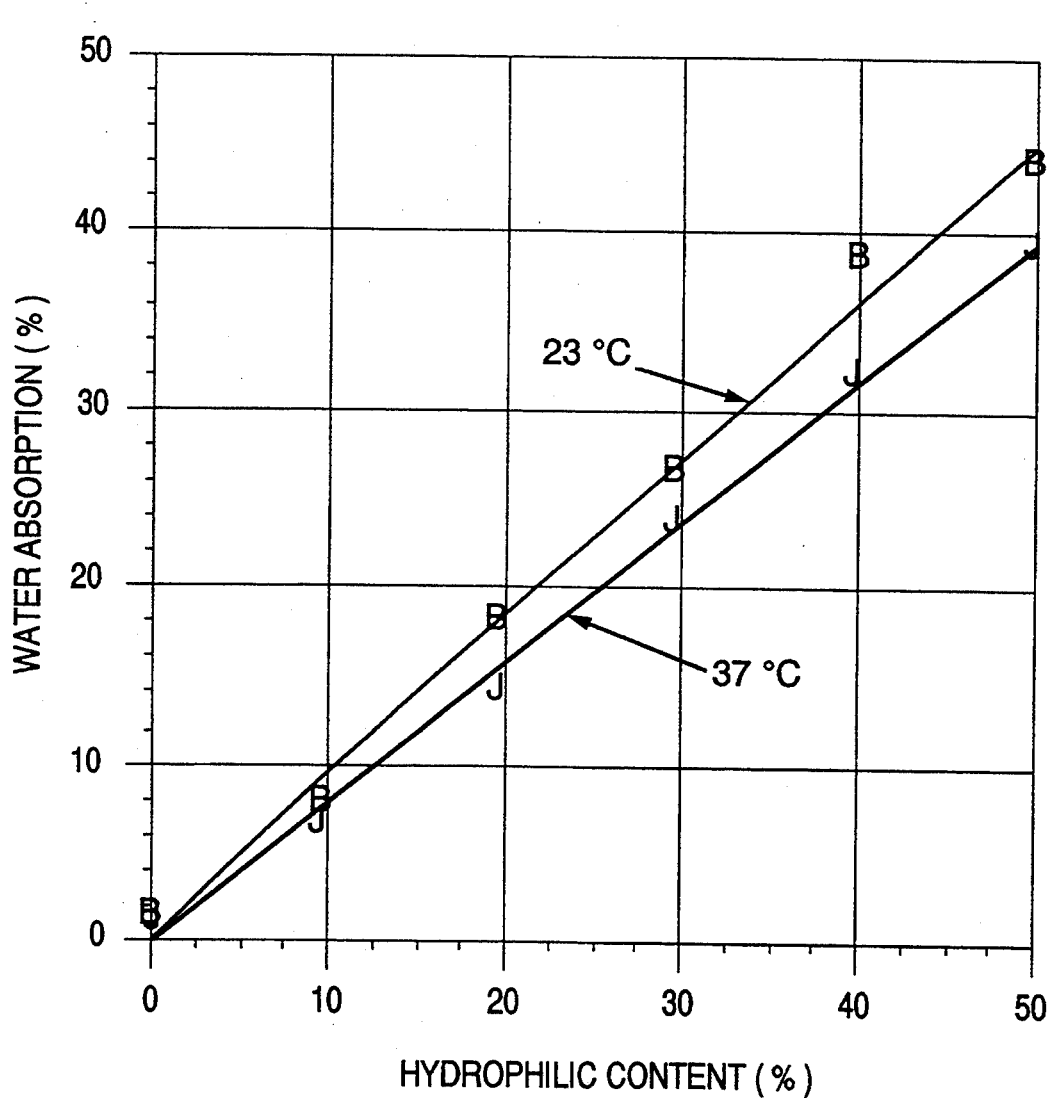
FIG. 3 is a representation of the variation of the capacity for water absorption of the membrane of this invention with increasing hydrophilicity.

Other objects, advantages and features of the present invention will become apparent to those skilled in the art from the following discussion.

DETAILED DESCRIPTION OF THE INVENTION

This invention arose from a desire by the inventors to improve on existing polymer technology to regulate, by varying certain parameters of the polymer composition, the permeability of the membranes obtained therefrom. Thus, by keeping the hard segment structure fixed, for example, the inventors have provided a co-polymer composition where they can vary the soft segment compostition, soft segment molecular weight and proportion thereof to the hard segment. The variation of these parameters provides a plurality of membranes of specifically tailored permeabilities.

This invention provides strong, biocompatible, hydrophilic segmented block polyurethane copolymers comprising a minor volume fraction of short hard segments and amphipathic or hydrophilic soft segments. Soft segment molecular weight, soft segment chemistry, and soft segment concentration may be chosen so that the resulting block copolymer absorbs sufficient water and the sum of the volume fraction of water and the volume fraction of hydrophilic soft segment exceed about 50% of the total volume of the water-swollen polymer. More preferable, the volume of absorbed water alone equals or exceeds about 50% of the total volume of the water-swollen polymer. In both cases the water-swollen polymer has an apparent continuous phase of hydrated soft segment and/or water which permits the permeation of macromolecules into, and through, the copolymer. This is particularly true when the copolymer is prepared in the form of a membrane, film or coating.

Although many of the copolymers disclosed herein possess hard segments which are polyurethanes or polyureas, the nature of the hard segment is a relatively unimportant determinant of the permeability of the resulting copolymers. Since the hard segments are essentially impermeable, their major function is to provide physical strength to the copolymer while existing as a separate molecular phase from the soft segment(s). In all cases maximum permeability to proteins and other macromolecules is achieved at minimum hard segment content. Therefore, when maximum permeability is required of the copolymer, its total hard segment is chosen to be no higher than required to provide sufficient strength for use in the intended application. Since hard segments other than polyurethanes and polyureas can often provide the required strength, it is within the scope of the present invention to employ copolymers with hard segments other than polyurethanes or polyureas.

Examples of suitable hard segments include those which when prepared as homopolymers have melting points (Tm) or glass transition temperatures (Tg) above 37° C. and preferably above about 60° C. in the dry state and which have melting points or glass transition temperatures above 37° C. in the fully hydrated state when initially hydrated at 20° to about 37° C.

Suitable hard segments have the optional requirement that, if present at sufficiently-high molecular weight and total concentration in the copolymer, they form a separate molecular phase from the soft segment(s) such that a distinct Tg or Tm is measurable in the copolymer, which must be within the above-specified range and which is also greater than the major Tg or Tm of the soft segments when the copolymer is fully hydrated. It should be noted that if the hard segment content is low and/or if the hard segment molecular weight is low, available instruments may be unable to detect the dominant thermal transition of the hard segment, hence the statement that detectability of Tg or Tm is an optional requirement.

Based on these requirements it can be seen that possible hard segments with the specified thermal transitions and water resistance which can be used in the present invention include a wide variety of chemical compositions. This is further illustrated by the following list of examples which is not intended to be all-inclusive or to limit the scope of the invention: aromatic and cycloaliphatic polyethers, polyesters, preferably aromatic polyesters, polyamides, polyimides, polycarbonates, polyolefins, polyacrylates, polydienes, polyacetals and other homopolymers, copolymers or multipolymers which have Tg or Tm greater than 37° C. in the hydrated state and preferably greater than about 60° C. in the hydrated state.

Furthermore, although essentially linear polyurethane(urea) copolymers are presented as exemplary copolymers, it is possible to achieve the required strength for certain applications by replacing some or all of the high-cohesive-energy hard segments with covalent crosslinks. Suitable crosslinks may be obtained through the use of multi-functional reagents employed in the synthesis or membrane casting steps and/or crosslinking may be achieved by a variety of methods known in the art which involve the use of various kinds of radiation to crosslink the polymer during or after it is converted to a configured shape, often through the inclusion of suitable reagents which become reactive when exposed to radiation. In polymers which derive significant strength from covalent crosslinks and posses little or no hard segment content, it is expected that hard segment Tg or Tm will be absent or unmeasurable by currently-available instrumental methods.

Furthermore, although essentially linear polyurethane(urea) copolymers are presented as exemplary copolymers, it is possible to achieve the required permeability and strength by incorporating branching or grafting along the backbone of the polymers of the present invention. One method of introducing branch points is through a combination of reactants having functionality greater than two together with monofunctional reactants. For example, a monofunctional polyalkyleneoxide may be reacted with a trifunctional isocyanate to produce a difunctional isocyanate with a pendant polyalkyleneoxide chain. The modified diisocyanate may then be used in the synthesis of a copolymer with branched or graft structure. Other methods of achieving branching and grafting are well known to those skilled in the art and are considered to be within the scope of the current invention.

Regardless of the hard segment chemistry or the presence or absence of covalent crosslinks, branch points or grafted side chains, the resulting polymer must retain sufficient water absorptivity and molecular weight between crosslinks (or molecular weight between hard segments defined later as "spacer length") to possess an apparent continuous aqueous phase in the fully-hydrated state. The exact hard segment content or crosslink density that is required to maintain a water-rich phase greater than about 50 vol % will vary for each specific polymer, but is easily measured gravimetrically by hydrating essentially dry polymer and noting the weight change if polymer density is known, or volume change upon hydration by displacement of a fluid of known specific gravity or direct measurement with, e.g., calipers. Polymers suitable for the practice of this invention will absorb sufficient water such that the total of the volume fraction of absorbed water and the volume fraction of the water-absorbing hydrophilic soft segments, which may be calculated from the density and weight fraction of hydrophilic soft segment present, exceeds about 50 vol % of the total volume of the fully-hydrated polymer. More preferable are copolymers which absorb sufficient water so that the volume fraction of absorbed water alone exceeds about 50 vol % and up to about 95 vol % of the total volume of the fully-hydrated polymer.

In the practice of the present invention the hard segment can also include a linkage between polyols or polyamines formed by a single diisocyanate without the use of chain-extending reagents.

While it is often desirable to use the polymers of the present invention in the form of films and membranes in unsupported form, it may also be useful to apply the polymers as coatings, laminations or impregnations to reinforcing substrates. Suitable substrates may be woven or knitted fabrics, microporous polymer structures, including integral microporous structures made of the polymers of the present invention, glass or carbon fiber mats and the like. These are known in the art and need not be further described herein. Particularly desirable substrates are expanded polytetrafluoroethylene, expanded polypropylene, expanded polyethylene, sintered ultra-high molecular weight polyolefins, carbon fiber fabrics, sintered carbon, woven dacron, knitted dacron, dacron velour and the polymers of this invention either as a separate substrate or as an integral part of the membrane. However, others are suitable as well.

Also provided herein is a non-porous, semi-permeable, optically-clear biocompatible film, membrane or coating formed from the block copolymer of this invention.

The optically-clear, non-porous, semi-permeable, film, membrane or coating formed from the block copolymer of this invention allows direct visual observation through the film or membrane. Also provided herein is a method of permeating molecules of molecular weights of up to about 6,000 to 600,000 daltons, and sometimes higher, while preventing the passage of condensed matter, and cells between two fluids, the method comprising interposing between the two fluids the non-porous polymer membrane, film or coating of this invention.

Chemistry, molecular structure and macroscopic structure affect the permeability and selectivity of a polymer membrane. Macroscopic structure, particularly the presence or absence of permanent pores, also determines the mechanism by which permeation will occur.

Two different mechanisms of permeation through membranes are discussed in the following paragraphs. These are the ones associated with non-porous or dense membranes and in microporous membranes.

In a microporous membrane, the passage of gases, vapors and solutes occurs through small capillary-like pores that inhibit the passage of larger molecules and cells, but which may eventually become clogged with oversized permeants restricting the passage of desirable permeants. Since microporous membranes have pores that are larger than the wavelength of visible light, they are invariably opaque or translucent in color, precluding the possibility of direct or microscopic observation of the contents of membrane containers. A non-porous or dense membrane acts in general as an absolute barrier to cells and other condensed phases of matter, but may be made selectively permeable to predetermined gases, vapors and/or solutes. Since dense membranes have no permanent pores that are larger than the wavelength of visible light, they can be water-clear or transparent in color. This is a very significant improvement over opaque microporous membranes, particularly in in vitro cell culture applications.

The mechanisms which provide selective permeability in microporous and non-porous dense membranes are quite different. As a result, the characteristics of these two types of membranes differ. For the purpose of this discussion, water-swollen membranes are considered to be dense if they are dense in their dry state. The inventors have found that permeation through pre-hydrated, water-absorbing membranes appears to follow simple Fickian diffusion kinetics as discussed below, even when a protein is the permeating species.

Non-Porous or Dense Membranes

It has generally been accepted that high molecular weight molecules could not pass through dense membranes due to their large size and/or low solubility in the membrane polymer. The following description of the phenomenon of permeation through dense membranes will explain the mechanism the inventors believe is responsible for permeation through the membranes of the present invention that are non-porous or dense membranes, and will clearly differentiate the membranes of the present invention from conventional microporous membranes.

In pinhole-free, dense polymeric membranes, it is known that the transmission of low molecular weight solutes, such as vapors and incondensible gases, occurs generally by activated diffusion. The driving force in activated diffusion is a concentration gradient within the membrane. The permeant first dissolves in the surface of the membrane on the side of highest concentration, and then diffuses across the film. Upon arrival at the opposite surface, the permeant desorbs and may then enter the surrounding space as a gas or vapor, or enter a liquid stream adjacent to the membrane's desorption surface.

The development of a concentration gradient within the membrane arises from a concentration difference in the phases that are in direct contact with each face of the membrane. The driving force for diffusion is the difference between the concentrations of permeant dissolved in the two faces of the membrane. For simplicity's sake, this is often reported as the concentration difference between the two adjacent phases. A linear relationship between the concentration of permeant in the phase in equilibrium with the film and the actual equilibrium concentration of permeant dissolved in the film, is assumed by Henry's Law, which holds for many polymers, to be represented by the mathematical equation $$c = sp \qquad (I)$$

wherein
 c is the concentration of permeant in the polymer film,
 p is the concentration of permeant in equilibrium with the film, and
 S is the solubility coefficient for the polymer.

In the simple case of the permeation of water through a dense membrane, made from nonpolar membrane polymers which absorb very little water, [e.g., polyethylene and polypropylene], $S_{H2O}$ is independent of p. For polymers which absorb larger amounts of water, S may change with p. In general, the solubility of the permeant in a dense membrane is an important determinant of permeability, because it establishes a maximum driving force that can exist within the film. Since solubility generally decreases as molecular weight of the solute increases, the solubility of proteins in any polymer membrane designed to permit their permeation is of particular importance. Fick's Law governs the rate of transport of the permeant through the thin film under the existing concentration gradient in accordance with the following mathematical equation $$q = -D\, dc/dx, \qquad (II)$$

wherein q is the amount of permeant diffusing through a unit area of the film per unit time, dc/dx is the concentration gradient across a thickness dx, and D is the diffusion constant for the specific polymer/permeant system.

If D is unaffected by the local concentration, c, then integration across the film thickness, l results in the following equation $$q = D(c_1 - c_2)/l, \qquad (III)$$

wherein $c_1$ and $c_2$ are the concentrations in the two surfaces of the film.

If $c_1$ and $c_2$ are related by Henry's law to the concentration of permeant in equilibrium with the two film surfaces, then equation (III) results in the equation (IV) below $$q = DS(p_1 - p_2)/l, \qquad (IV)$$

wherein the product of the diffusion constant D and Henry's Law constant or solubility coefficient, S, is known as the permeability constant p. Thus, equation (IV) is equivalent to equation (V) below.

$$p = DS = ql/(p_1 - p_2), \qquad (V)$$

wherein p has units of volume times thickness divided by area, driving force and time. It can be clearly seen from equation (V) that the rate of permeation depends on both the diffusivity D and solubilty S of the permeant in the membrane polymer.

The p values for many polymer/permeant pairs may be found in the literature, but only for cases in which the permeant is a relatively low molecular weight gas, vapor or solute. No such values are available for the permeation of proteins through dense polymer membranes.

A simple inspection of equation (IV) reveals that the permeation rate of a specific non-porous film is directly proportional to the concentration difference and film area, and is inversely proportional to the film thickness.

In the design of a membrane polymer for use in the present invention the permeability coefficient, p, may be maximized through changes in polymer chemistry or structure which maximize D and S for the desired permeant. These changes will increase both the water uptake and the segmental mobility of the polymer.

Our finding that a dense membrane in which water or a water-swollen hydrophilic soft segment phase comprises a major component, e.g., greater than about 50 vol %, protein diffusion rates may be comparable to, although lower than their diffusion rates in water is an important aspect of the present invention. High equilibrium water content may significantly increase protein solubility in the hydrated membrane relative to the membrane's dry state. Since dense-membrane permeability depends on both the diffusivity and the solubility of the permeant in the membrane phase, a membrane polymer with high water content may be permeable to high molecular weight, water-soluble permeants by presenting a water-like continuous phase through which the permeant may easily pass (diffusivity enhancement) and an aqueous environment in which the permeant may easily dissolve (solubility enhancement).

Some polymer properties influencing the permeability constant are discussed below.

Crystallinity

Crystalline polymers are generally considered to be completely impermeable. In semicrystalline polymers, an increase in crystallinity produces a decrease in permeability. This effect can be quite significant at the phase inversion point when the continuous phase, which is usually the phase present at >50% volume fraction, changes from amorphous to crystalline. Certain membrane polymers of the present invention may also form impermeable crystalline regions within the soft segments when the membrane polymer is in the dry state. On hydrating, however, we have found that these crystalline regions become amorphous and readily permit the passage of relatively high molecular weight permeants.

Glass Transition Temperature

An amorphous polymer will be more permeable as a rubbery material at a temperature above its glass transition temperature (Tg) than in its glassy state below Tg. Silicone rubber, for example, has a Tg of −120° C. When at room temperature, it is 140° C. above its Tg, and it is, therefore, extremely permeable to a number of gases and vapors. Silicone is virtually impermeable to water-soluble permeants of high MW, however, since its hydrophobicity results in very low solubilites of permeant in the polymer, which absorbs little or no water. In segmented polymers, such as polyurethaneureas, where the hard segment is glassy or crystalline and the soft segment is rubbery, permeation occurs primarily through the rubbery phase. If the content of hard segment is increased to a point where it becomes the continuous phase, the permeability coefficient, p, drops significantly. An important aspect of the polymers of the present invention is that the soft segment Tg is relatively low due to the choice of reactants and due to the placticizing effect of absorbed water and that the impermeable hard segments comprise a minor volume fraction of the water-swollen polymer.

Affinity & Solubility Parameters

The greater the solubility of a permeant in the hydrated polymer, the greater the concentration gradient of permeant that may exist within the polymer. The difference between the solubility parameters of the permeant and the polymer is one way of expressing this property. However, specific interactions normally exist between the polymer and the permeant which make any predictions based solely on the solubility parameter less than accurate. One such specific interaction involves hydrogen bonding between (water-swollen) polymer and permeant. More specifically, reversible hydrogen bonding among water molecules, chemical groups on the polymer, and chemical groups on the permeant molecules may play an important role in facilitating permeability of proteins through dense membranes of the present invention.

As indicated above, the chemical structure of a polymer may be varied, and this variation may be used to maximize the permeability of a dense film made from that polymer to a specific permeant. However, at the present time, an understanding of the exact relationship between the structure of the polymer and the permeant selectivity obtained by a membrane during solute separation is lacking. Any a priori prediction of permeability, thus, remains difficult.

Crosslinking

Crosslinking generally decreases the permeability of a membrane, particularly to large molecules, such as proteins. At low crosslink density, however, the permeability of low molecular weight solutes may be only slightly affected. The crosslinking of polyurethanes, for example, may be the result of certain side reactions during polymer synthesis which form allophanate and/or biuret groups, the reaction of polyfunctional reagents to form urethane or urea groups, or because of exposure to radiation. For any of these cases, high levels of crosslinking may have a significant negative effect on the permeation coefficient of proteins and other macromolecules, although low to medium levels may be useful in enhancing the strength of the membranes, particularly in the hydrated state. It is an important feature of the present invention that the amount of crosslinking in membranes, films and coatings be kept low enough so that the previously-stated water absorption requirements are met.

Orientation

Stretching and orienting a film generally reduces its permeability constant p, primarily because of denser molecular packing or increased crystallinity, which occur as a result of the orientation.

Other

A substantial sorption of water by a polymer film increases the diffusion constant D due to swelling and plasticization. Thus, water absorption by the membrane polymers of the present invention can increase permeability by both Tg-lowering plasticization, and by a reduction in crystallinity of the hydrophilic domains relative to their crystallinity in the dry state. The affinity, or solubility, S, of the water-swollen polymer to water-soluble permeants such as proteins is also related to polymer water absorption, since a water-swollen soft segment capable of hydrogen bonding with sorbed water, will appear to the permeant to be more water-like than the dry polymer.

Segment Molecular Weight

The present inventors have found that by carefully choosing the soft segment chemistry to enhance water absorption, and by limiting the (impermeable) hard segment content such that it comprises a minor volume fraction of the water-swollen polymer membrane, protein permeability may be achieved. The present inventors have also found that an additional structural variable is important in determining the upper molecular weight of solutes which will permeate through the polymer membrane (i.e. selectivity): segment molecular weight or, more precisely, segment molecular length.

As previously mentioned, the soft segment comprises the permeable, but weak phase of the membrane polymer. The hard segment comprises the strong, impermeable phase of the membrane polymer. The much higher cohesive energy density of the hard segment gives it the ability to add strength to the overall polymer, but contributes essentially no permeability to the polymer (membrane). Thus it may be assumed that all permeation occurs through the soft segment. It has also been mentioned that the most effective hard segments are those with the best phase separation from the soft segment. That is, on a molecular scale, the most desirable hard segments are those that separate into domains containing like hard segments on adjacent polymer chains, while the soft segments comprise a separate phase. In an aqueous environment, the soft segment will also contain an amount of absorbed water which can vary from nearly zero to very high levels, depending on the inherent hydrophilicity of the soft segment oligomers.

Since the soft segment oligomers are, on average, covalently bonded at each end to a hard segment, it is clear that the maximum spacing possible between the impermeable hard segments is related to the length of the soft segment oligomer. Thus a critical molecular dimension for permeation of large molecules is set by the average soft segment molecular length. For essentially linear soft segment oligomers, molecular length is directly proportional to molecular weight. It follows then that increasing soft segment oligomer molecular weight should increase the maximum molecular weight of solutes which may permeate through the polymer. This effect may be applied to tailoring membrane permeability by choosing soft segment oligomer molecular weight. A typical commercially-available polyether oligomer, for example, may be obtained in molecular weights ranging from a few hundred to a few thousand daltons. To achieve molecular weight cutoffs higher than those obtainable with commercially-available soft segment oligomers, another approach is possible. Available soft segment oligomers may be coupled together prior to the reaction used to synthesize the final membrane polymer.

In polyurethane synthesis, a so-called three-step reaction can be employed in which the first step involves covalently bonding two or more oligomers together while optionally retaining the oligomer's original endgroups by appropriate control of the stoichiometry of the coupling reaction. For example, three moles of hydroxyl-terminated polyether oligomer might be reacted with two moles of a diisocyanate chosen to be different from the isocyanate used in the hard segment of the final polymer. Using a different diisocyanate to couple soft segment oligomers is optional but preferable since it minimizes the association of the coupling segment with the hard segment of the polymer. This is the desired situation for maximum permeability. In this example, if the original polyol molecular weight was 2,000 daltons, the coupled oligomer would have an average molecular of 6,000 plus the molecular weight of the two diisocyanates used in the urethane-forming coupling reaction. When this coupled oligomer is subsequently reacted to form the final membrane polymer, the maximum end-to-end distance between hard segments would be increased more than three times, relative to the original 2,000 molecular weight oligomer before coupling.

The maximum end-to-end distance of the optionally-coupled soft segment oligomer is referred to herein as a "spacer length". In the inventors' theoretical model of the membrane polymer, the spacer length is a determinant of the upper molecular weight cut-off of the membrane polymer. The relationship between the maximum permeant molecular weight which can pass through a membrane may not be a linear function of the spacer length. A permeant which assumes a roughly spherical conformation might increase its spherical diameter in proportion to the cube root of its molecular weight. A rod-like permeant, on the other hand, might increase its major dimension in direct proportion to its molecular weight. Furthermore, there is additional uncertainty associated with the relationship between average distance between impermeable hard segments and the molecular weight/length of the soft segment oligomer "spacers". It is likely that in the dry membrane polymer the soft segment oligomers assume a somewhat random coil conformation, or they may be folded into crystalline domains. Upon water immersion and absorption, if there is significant water uptake and optional vitrification of the soft segment crystalline regions, a volume increase will result. As the polymer membrane increases in volume, the now amorphous, coiled oligomers may assume a more linear conformation, making average spacer length closer to the soft segment oligmer end-to-end distance. An additional effect of increased soft segment molecular length may be that longer chain length between hard segments permits the formation of a smaller number of hard segment domains, albeit of larger size. This effect could be caused by increased mobility of hard segments tethered through covalent bonds to very long soft segment spacers. For a spherical hard segment domain, domain volume increases with the cube of the diameter. A small increase in domain diameter may result in a large decrease in the number of hard segment domains impeding the transport of high molecular weight solutes, resulting in an increase in permeability to high MW permeants.

Short hard segment length enhances permeation of high MW solutes for the same reason that long soft segment length does. It is therefore desirable to minimize hard segment length. This must be done without decreasing total hard segment content, e.g., weight fraction of hard segment, below a critical minimum, since the strength of the polymer decreases with total hard segment content. For a given hard segment content and soft segment molecular weight, the hard segment length is minimized at maximum membrane polymer molecular weight. Too high a molecular weight, however, causes fabrication difficulties due to excessively-high melt or solution viscosities. In the present invention, membrane polymer molecular weight is controlled by chain-stopping through the addition of monofunctional reagents to the reaction mixture, or through the use of a stoichiometric imbalance of one of the reactants. Furthermore, by selecting certain hydrophilic monofunctional chain-stoppers the permeability of the polymers of the present invention can be enhanced. This may be attained by adding to the total hydrophilic content of the polymer while also limiting molecular weight to a desired range.

The polymers of the present invention may be synthesized to have a specific permeability to a given permeant and/or to have a specific molecular weight cutoff, by implementing an empirical, yet systematic approach. The empirical nature of the method is mandated by the nature of the phenomenon of permeability through dense membranes, the properties of specific permeants or non-permeants, including their solubility properties, molecular size and conformation. The inventors provide herein a systematic approach to the production of membrane polymers in accordance with the present invention, which may be used to tailor membrane properties for specific applications. This is described briefly in the following paragraphs.

The permeation of solutes through dense polymeric membranes is determined for the most part by the diffusivity and solubility of the permeants in the membrane polymer. If the membrane polymer absorbs a significant amount of the solvent, then the permeation of the solutes will be determined by the diffusivity and solubility of the permeants in the solvent-swollen membrane polymer.

The absorption of a solvent, e.g., water, by the membrane polymer requires that the polymer have some affinity for the solvent. In addition, by definition, the solvent must be capable of dissolving the solute/permeant. It follows, thus, that the absorption of the solvent by the membrane may increase contribution of the solubility factor to the permeability coefficient by making the environment within the membrane polymer more like the pure solvent than it was in the dry state.

In general, in addition to enhancing the solubility of the permeant in the membrane polymer, a low molecular weight solvent will often act as a plasticizer for the membrane polymer. Plasticization involves a degree of dissolution of the polymer by the plasticizer. Furthermore, as the level of plasticizer/solvent increases, the glass transition temperature of the mixture will generally decrease. A decreased glass transition temperature suggests that the plasticizer may facilitate the relative movement of macromolecular chains by inserting themselves between adjacent chains to increase the intermolecular spacing there between. In addition to the above, plasticizer/solvents may reduce the degree of possible polymer-polymer interactions through specific interactions between the polymer and the plasticizer/solvent. A reduction in the soft segment crystallinity upon hydration, which occurs with certain membrane polymers of the present invention, is an example of the latter mechanism.

In the case of an isotropic polymer membrane, significant solvent absorption/swelling will produce a measurable increase in the physical dimensions of the membrane, e.g., along each of the x, y and z axes, by an amount approximately equal to the cube root of the volume fraction of the solvent absorbed therein. This provides direct evidence that the polymer chains have increased intermolecular distance in the swollen state since the same number of polymer molecules are now contained in a larger total volume. This increased spacing and facilitated movement of polymer chains may increase permeability by increasing the diffusivity contribution to the permeability coefficient.

Thus, the absorption of a solvent by a membrane polymer may enhance the membranes permeability by increasing both the diffusivity and the solubility of a particular permeant. One method of tailoring the membrane of the present invention to obtain a specific permeability rate and/or molecular weight cutoff, is to vary the composition and morphology of the membrane. This will effect an enhancement of the amount of solvent absorbed, and of the extent of solubility and diffusivity that results from greater solvent absorption.

Although in some instances it may not always be possible to make exact quantitative predictions of the permeation characteristics of the resulting membrane, the inventors have found that certain qualitative and quantitative relationships exist which guide the process. Furthermore, the permeability of candidate membranes may be performed with the methods described by the inventors herein. The structure vs. property relationships provided herein may be used to adjust the permeability properties of the membrane through an iterative process of synthesis, membrane casting and permeability measurement, until the desired values for the intended use are attained.

In the examples provided in Table 4 below it is assumed that the permeant is a water-soluble macromolecule and that the solvent is water or an aqueous fluid. Those skilled in the art will know that similar approaches may be applied that are suited for other solvent/permeant systems by modifying the soft segment to facilitate the absorption of a non aqueous solvent, for example.

increases and strength decreases with total porosity or void volume fraction.

The application of microporous membranes to the concentration-driven transport of large molecules, such as proteins present in a medium, poses several problems. Since only the pores of the membrane are available for the mass transfer of large molecules, the fraction of the total area of the membrane available for permeation is limited. This slows the rate of transfer of molecules across the membrane. Porous membranes which work well in pressure-driven separation such as ultrafiltration, exhibit much lower permeation rates when used in concentration-driven processes in which pressure is not or can not be applied to the upstream side of the membrane. Usually, highly porous membranes also lack strength and present a rough surface to blood and tissue alike. Furthermore, the pores become easily clogged by the adsorption of a protein or, in blood-contacting applications of the membrane, a build-up of a thrombus or fibrin mat. All these effects dramatically reduce transport rates. A reduced transport rate is likely to slow the response of cells placed on the other side of the membrane and may even produce an undesirable out-of-

TABLE 4

Membrane Polymer Structure Versus Property Relationships

| Variable | Effect |
| --- | --- |
| Increasing Soft Segment Molecular Weight | Increases water absorption at constant soft segment hydrophilicity and constant soft segment content (++) <br> Increases permeability rate (+++) <br> Increases molecular weight cutoff (++) <br> Increases (dry) soft segment crystallinity (++) <br> Decreases (dry) tensile modulus unless soft segment crystallizes (−) <br> Increases ultimate tensile elongation unless soft segment crystallizes (+) |
| Increasing Soft Segment Hydrophilicity | Increases water absorption at constant soft segment molecular weight and constant soft segment content (+++) <br> May increase soft segment crystallinity if hydrophilic segments crystallize (++) |
| Increasing Hard Segment Content | Decreases permeability rate (− − −) <br> Increases tensile strength (++) <br> Increases tensile modulus (+++) <br> Increases wet strength (++) |
| Increased Hard Segment Domain Size | Increases permeability rate at constant hard segment content (+) |
| Mixing Two or More Soft Segments | Increases permeability rate when it decreases soft segment crystallinity (++) <br> Can be used to increase solubility of permeant in polymer (by adding groups which have an affinity for permeant) and therefore increases permeability (++) |
| Crosslinking At Low Crosslink Density | Increases permeability if used to obtain strength by significantly reducing hard segment content. (++) <br> Can decrease permeability rate and molecular weight cutoff at higher crosslink density (− − −) |

(+) and (−) refer to the nature of the effect and its intensity:
(+++) = Strong positive effect.
(−) = Weak negative effect, etc.

Microporous Films

When permeation occurs by transport through "large" pores, e.g., greater than about 0.1 micron, the transmission rate through a microporous membrane is generally directly proportional to the film area and the concentration driving force. However, the transmission rate is affected far less by the thickness of the film than it is in monolithic films. On the other hand, the porosity of a microporous membrane is a major determinant of the permeability rate. A microporous membrane made from polyethylene, polycarbonate, polyvinylchloride or other polymers and copolymers which are glassy or crystalline at the use temperature, e.g., 37° C., will transport polar permeants primarily through its pores. For that type of membrane, therefore, permeability phase/positive-feedback of, e.g., insulin release, at low glucose levels, in the case of glucose-sensitive insulin-producing cells. As the transport of nutrients and other necessary molecules is further reduced, the cell viability will become threatened. Dense membranes lacking pores, having therefore microscopically smooth surfaces, in accordance to this invention, reduce or eliminate these problems.

The careful consideration of the known properties of various types of biocompatible polymers, and the inventors' experience with urethanes in particular, led to the utilization of polyurethanes for the preparation of copolymers that are flexible, strong, biocompatible, nonporous, and inexpensive and which at the same time have specific permeability characteristics. By practicing the present invention, the quality, safety and efficacy of the product is assured. The development of the present polyurethane was undertaken to ensure the attainment of desirable strength and elastomeric properties along with high quality, safety and efficacy of any films and membranes produced therefrom.

The following paragraphs will mostly refer to a copolymer of 4,4'-diphenylmethane diisocyanate (MDI), polytetramethylene oxide (PTMO), and ethylene diamine (ED). The copolymer will serve to exemplify the invention which is not limited to it. The chemical structure often used to represent a polyurethaneurea obtained by a reaction of MDI, PTMO, and ED, a copolymer of this invention, is structure (2) in Table 5 below. However, the information provided herein by means of example is applicable in general to all copolymers in accordance to this invention. This, therefore, applies to hard segments other than the ones exemplified.

ether oxygens in the soft segment increases. Ether oxygens are the preferred hydrophilic group for the practice of the present invention, especially the ether oxygens present on the polyethyleneoxide (PEO) and PEO-containing copolymers, multipolymers and blends.

When PEO homopolymers are used as the sole soft segment, it is particularly preferred to use high molecular weight oligomers, preferably above about 1,000 daltons, and most preferably above 3,000 daltons, for the reasons already stated. PEO ether oxygens readily absorb and hydrogen bond with water, without giving rise to a permanent adsorption of the permeants, which would otherwise retard or prevent permeation through the membranes of the present invention. On the other hand, it is possible to utilize other hydrophilic groups in the soft-segment for practicing of the present invention, including hydroxyl, carboxyl and/or other ionic groups

TABLE 5

Structure of Four Exemplary Polyurethanes of Increasing Hydrophilicity

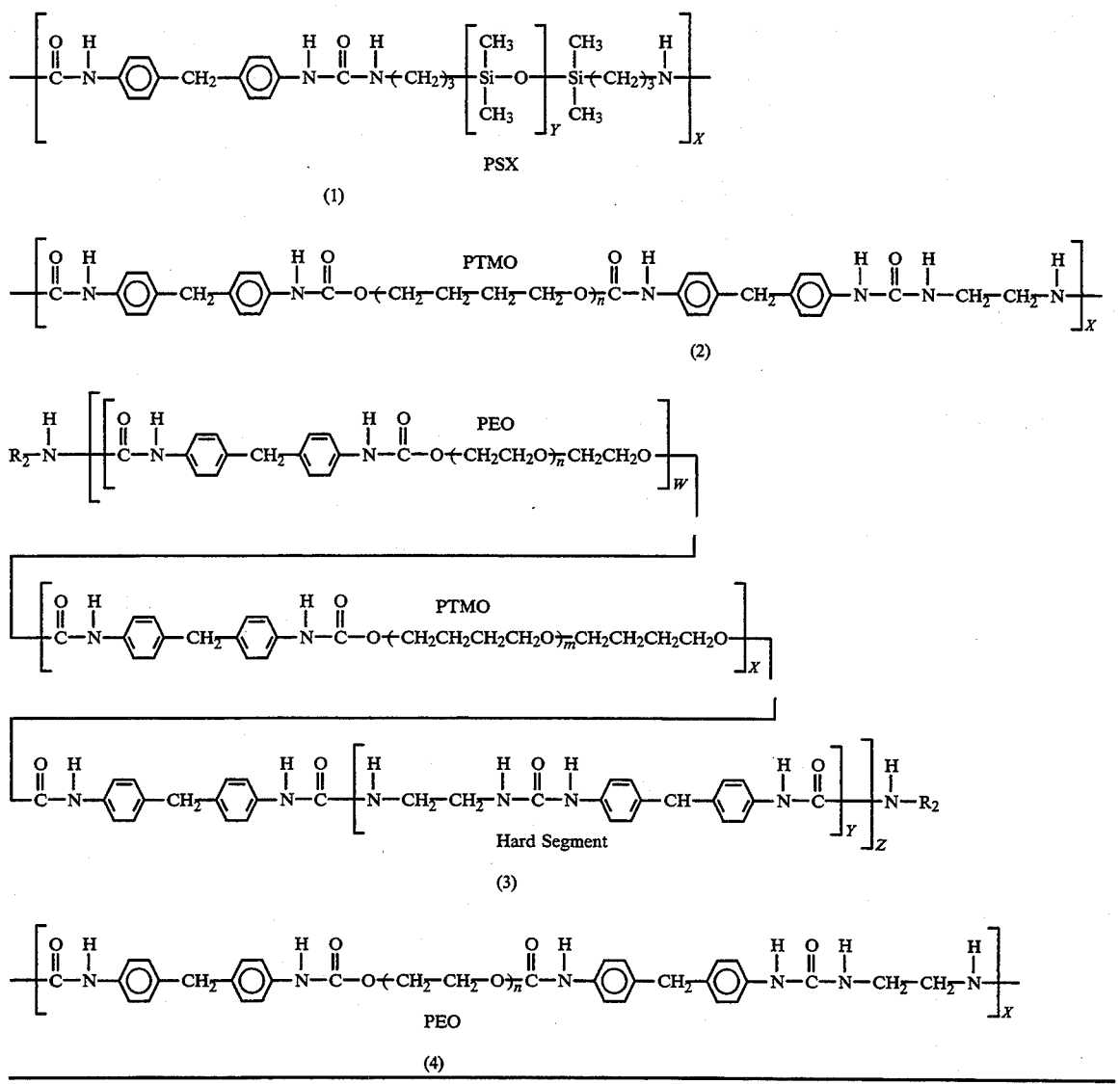

PSX = polydimethylsiloxane (i.e. silicone),
PTMO = polytetramethyleneoxide
PEO = polyethyleneoxide In the last three structures of the series ((2), (3), and (4)), the hydrophilicity increases as concentration of alone, or in various combinations, to achieve a desired water absortivity.

The copolymers of the invention may be prepared by one-step, two-step or three-step synthetic methods depending on the complexity of the chemical structure desired. Examples of polymers prepared by all three methods are provided below. The one-step method is exemplified in Table 6 below.

ple cited above, the end groups on the polymer may vary depending upon which polyol reacts with the isocyanate e.g., (MDI) and the exact stoichiometry of the reaction mixture. The end group could be butanediol (—OH), polyethylene oxide (—OH), or isocyanate (—NCO) residues.

The two-step method is exemplified in Table 7 below.

TABLE 6
Polymer Obtained From a MDI/BD/PEO One-Step Synthesis

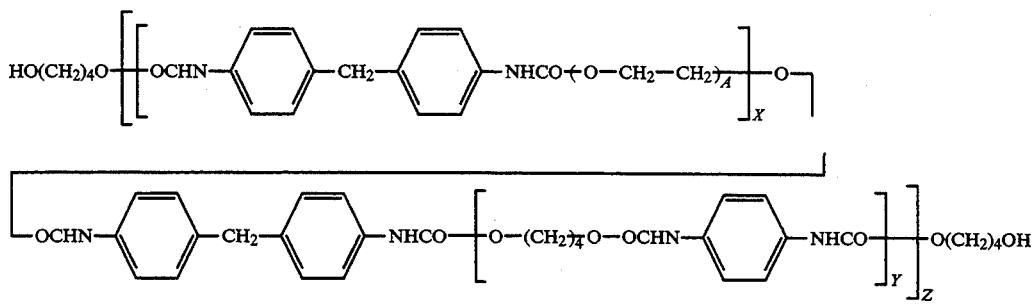

wherein
A is about 4 to 23000, preferably about 4 to 180;
X is about 1 to 25, preferably about 1 to 15;
Y is about 1 to 20, preferably about 1 to 10;
Z is about 1 to 20, preferably about 1 to 10;
and
the end groups may vary.

TABLE 7
A MDI/ED/DBA/PEO/PPO—PEO Polymer Prepared by Two-Step Synthesis

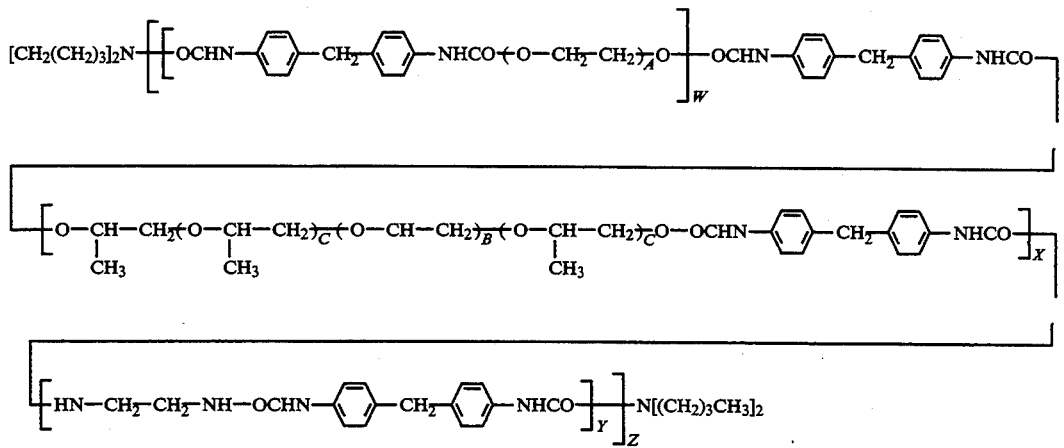

wherein
A is about 1 to 23000, preferably about 4 to 180;
B is about 4 to 400, preferably about 4 to 200;
C is about 1 to 100, preferably about 4 to 75;
W is about 1 to 25, preferably about 1 to 15;
X is about 1 to 25, preferably about 1 to 15;
Y is about 1 to 20, preferably about 1 to 10;
and
Z is about 1 to 20, preferably about 1 to 10.

The PPO—PEO polyol may be either a block or random copolymer.

In the one step synthesis, all the reactants are added to the reaction chamber at the same time. In the exam- The three-step method is exemplified in Table 8 below.

TABLE 8
A TDI/PEO/MDI/ED/DBA Polymer Prepared by Three-Step Synthesis

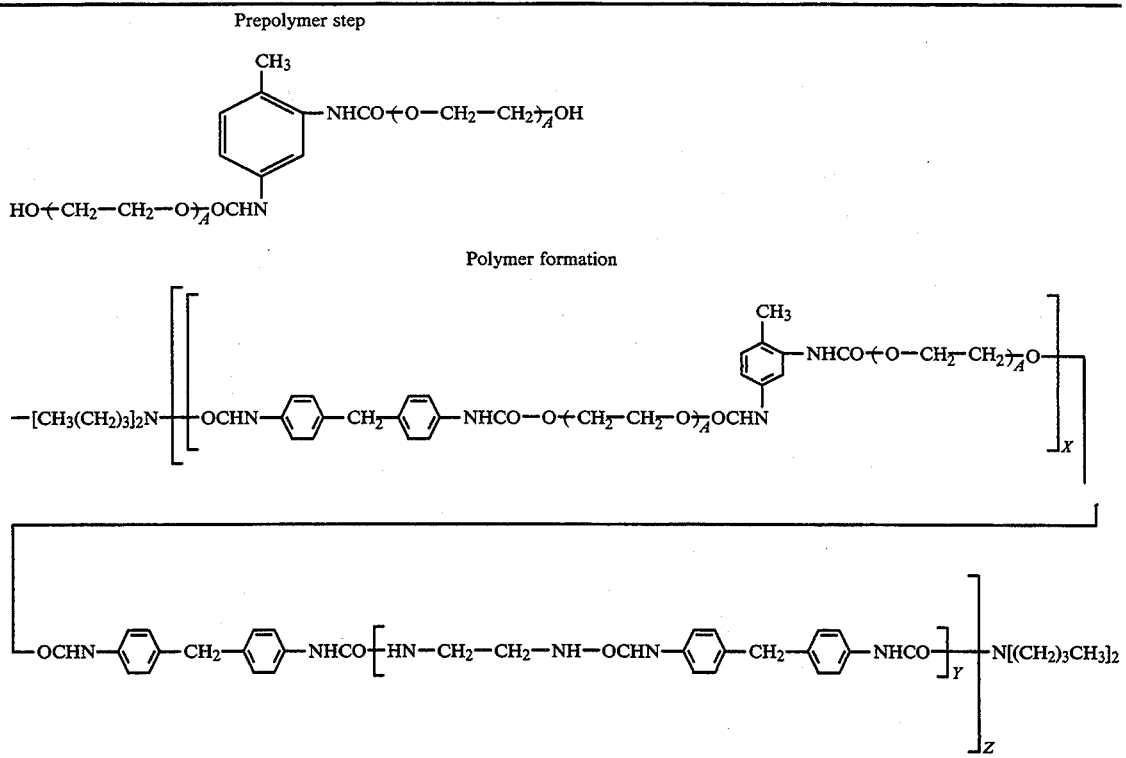

wherein
A is about 4 to 23000, preferably about 4 to 180;
X is about 1 to 25, preferably about 4 to 15;
Y is about 1 to 25, preferably about 4 to 15;
and
Z is about 1 to 20, preferably about 4 to 10.

As already indicated, the synthetic pathways of these methods will be generally discussed by reference to the particular examples provided. However, an artisan would know how to extend the knowledge acquired herein to the synthesis of other copolymers in accordance with this invention. The exemplified prepolymer, for example, may be made using a combination of different polyols or polyamines or mixtures thereof.

By means of example, in a two-stage reaction, the DBA, PTMO and the MDI may be first reacted to form an isocyanate-terminated prepolymer. Preferred conditions for this step are as follows. The prepolymer may then be chain extended with ethylene diamine (ED) at low temperatures, such as about 0° to 70° C., and preferably about 5° to 10° C., to give a high molecular weight, segmented polymer. In a typical solution polymerization, e.g., using urethane-grade reactants and reagent grade solvents, enough water may be present as an impurity to consume a significant portion of the isocyanate groups present. This reaction will generate carbon dioxide and a urea group, that will couple two MDI residues with no methylene groups there between. These structures will be present in proportion to the amount of water present in the reactants and solvent. The hard segments produced in each reaction may be expected to contribute differently to the properties of the polymer, e.g., by changing the degree of phase separation from the soft segment. Many other reactions, such as side reactions, further complicate the structure of the polymer of the invention, thus making any simple representation of the copolymer approximate. The side reactions may create difficulties for any prediction of structure vs. property relationships as well as increase the likelihood of batch-to-batch variations in the characteristics of the copolymer of the invention. The use of pure, dry reactants and anhydrous reaction conditions, and the use of chain-terminating reagents aids in the control of the overall polymer molecular weight minimizes side reactions and gives polymer structures more closely approximating the ideal or theoretical structure.

In the development of the polyurethane copolymers of the invention, the elastomers are designed to have excellent physical characteristics, such as toughness and elongation. In addition, the copolymers of this invention are designed as a family of materials with a broad range of modulus and hardness that may be tailored for many particular applications. Although tailoring of permeability properties of the copolymer of this invention is often of primary importance, within the structural constraints of the required permeability, it is also possible to tailor physical properties as well. In most cases the polymers of the present invention will have the desired protein and/or macromolecular permeability and also possess excellent physical properties as well. The fact that excellent physical properties can be obtained is of particular importance in maintaining barrier properties of the membranes, i.e., exclusion of unwanted cells and high molecular weight permeants. A high level of toughness when compared to certain gels and hydrocolloids permits the copolymers of the present invention to be fabricated into many useful shapes while still maintaining physical integrity of the membrane. Of particular importance is the ability to fabricate very thin, unsupported membranes, often less than 30 μM in thickness. The importance of thickness in determining necessary permeation rate has been described above. Some typical physical properties of membranes of the present invention are listed in Table 9 below.

TABLE 9

Characteristics of Copolymers of Invention (Measured Dry)

| Characteristic | Value |
| --- | --- |
| Tensile Strength | $\geq \approx 350$ psi |
| Elongation at Break | $\geq \approx 300\%$ |
| Initial Modulus | $\approx 75$ to 20,000 psi |

Because of an interest in preparing polyurethanes of different moduli, the relationship between modulus and total hard segment content is sometimes important. For the polyurethanes of the present invention, the hard segment content is defined herein as the weight of diisocyanate plus chain extender, and hydrophobic chain terminator, if present, divided by total polymer weight. A linear proportion is found between initial, i.e., measured at less than 10% strain, modulus and hard segment over a range of about 9 to 30% hard segment content. Linear, not crosslinked, elastomers of about 9% hard segment and below have properties similar to unvulcanized rubber and are, therefore, not of particular interest for the present use as unsupported films or membranes. They may be used, however, as coatings or impregnations on porous reinforcing substrates.

At high elongations, the pure soft segment may undergo reversible crystallization, giving an increased modulus and a somewhat reduced ultimate elongation. The thus resulting polymer also possesses excellent strength and certain other desirable properties.

TABLE 10

Copolymer Characteristics

| Characteristics | Range |
| --- | --- |
| Tensile strength | > about 350 and up to about 10,000 psi |
| Elongation at Break | > about 300% and up to about 1,500% |
| Water Absorption + Hydrophilic Soft Segment | > about 100% and up to > about 2,000% dry wt > about 50% and up to about 95% wet weight |
| or more preferably: | |
| Water absorption only | 100% and up to > about 2,000% dry wt about > about 50% and up to about 95% wet weight |

The diisocyanate and all reactants which contribute an active hydrogen, i.e., polyols, diamine, amines, may be added in a proportion of about 0.9 to 1.2 and more preferably about 0.95 to 1.1. The reactants may be added to a solvent of the following characteristics.

Suitable solvents are organic solvents that partially or completely stabilize or suspend the various reagents utilized in the preparation of the polymer. Preferred solvents are generally polar liquids and may include, but are not limited to, dimethylacetamide, dimethylformamide, dimethylsulfoxide, 2-methyoxyethanol, n-methylpyrrolidone, pyridine, and tetrahydrofuran. Combinations of these solvents may also be used.

The solution of diisocyanate and polyalkylene oxide in a solvent is preferably about 40 to 85 wt % solids, more preferably about 50 to 80 wt % solids, and still more preferably about 75 wt % solids. However, it may be varied within a broader range.

The polyalkylene oxide reagent typically has a molecular weight of about 200 to 9,000, although other ones may be utilized.

The diisocyanate may be an aromatic or an aliphatic polyisocyanate. The diisocyanates may be selected from the group consisting of alkyl diisocyanates, arylalkyl diisocyanates, cycloalkylalkyl diisocyanates, alkylaryl diisocyanates, cycloalkyl diisocyanates, aryl diisocyanates, and cycloalkylaryl diisocyanates, which may be further substituted with oxygen, and mixtures thereof. However, others are also suitable.

The reaction may be conducted at a temperature of about 50° to 130° C., and more preferably about 55° to 60° C. for aromatic isocyanates and about 100° to 110° C. for aliphatic isocyanates, and a pressure of about 0.1 to 100 atm, and more preferably about 0.1 to 10 atm. Preferred are atmospheric pressure and an atmosphere free of moisture and oxygen.

The reaction will in general go to completion in about 3 hours, and it may be conducted with agitation.

The thus obtained polymer or prepolymer will, in general, have a molecular weight of about 300 to 1,000,000, and more preferably, about 5,000 to 60,000.

The reagents and solvents should preferably be of high purity if the best results are desired. However, other grade reagents and solvents may also be utilized.

In general, as indicated above, the synthesis of polyurethanes is affected by moisture. Accordingly, all equipment utilized for synthesizing the copolymers of the invention should be thoroughly dried before use. All steps of the preparation thus should, in general, be maintained substantially water-free. Caution, in addition, should be exercised not to expose any reactants or solvents to atmospheric moisture. Moreover, some of the substances utilized for the synthesis of the copolymers of the invention, such as diphenyl methane diisocyanate (MDI), are highly toxic. Accordingly, the use of a respirator and gloves and adequate mechanical ventilation is recommended when handling them. Combustible solvents, such as dimethylformamide, which are suitable for use herein, are absorbed through the skin. Accordingly, any vapor breathing and skin contact with these compounds must be avoided.

One general procedure for preparing the copolymer of the invention is as follows. The polyols may be blended together under essentially anhydrous conditions, preferably under vacuum and a nitrogen atmosphere at a temperature of about 100°–110 ° C. until their water content is, e.g., less or equal to about 250 ppm. This value is usually attained in about 1 to 1.5 hours. A clean, dry nitrogen-purged reactor may then be filled with the dry polyol blend. A polyol or polyamine, such as dibutyl amine may then be accurately weighed and added to the reactor, and a solvent, such as dimethylformamide (DMF), may be added to a concentration of about 40 to 85% solids, and more preferably about 75% solids to form a pre-polymer, and the mixture may then be stirred, e.g., at about 30 to 40 rpm. A diisocyanate, such as 4,4'-diphenylmethane diisocyanate (MDI), may be added at this point. The content of the reactor may then be heated to about 60° C. with a variation of about 2° C. The reaction is then allowed to continue for, generally, about 3 hours at this temperature, noting the temperature at regular intervals throughout. At the end of the 3 hours, the reaction is stopped by cooling, e.g., in an ice bath. The temperature of the solution at this point should be about 15° C. with a margin of 2° C. for starting the chain extension reaction. The thus obtained pre-polymer may be diluted to about 25% in an organic solvent, such as DMF, with a margin of error of about 2%. Samples may be removed from the reactor at different times for titration to determine the amount of isocyanate in order to assess readiness for ethylene diamine addition according to the following protocol. The figures provided are exemplary, but similar calculations may be conducted for different volumes and amounts of substrate to be titrated.

The percent of solids of the prepolymer in the reaction vessel is calculated from the recorded additions. A derivatizing solution may be prepared by adding 7.5 grams of dibutylamine to a dry 250 ml volumetric flask and diluting to the mark on the flask with the same organic solvent used in the synthesis. Three 5 gram (nominal) samples of the prepolymer may be accurately weighed, and each placed into a separate Erlenmeyer flask with a dry magnetic stir bar. 20 ml of the derivatizing solution may be added to each sample using a 20 ml volumetric pipet. The flask may then be covered with aluminum foil and stirred for 20 minutes at room temperature. 50 ml of isopropyl alcohol (IPA) and six drops of bromophenol blue indicator may be added. A buret may be filled with 1.0N aqueous HCl. The solution may then be stirred and titrated with 1.0N aqueous HCl to a yellow end point, and the amount of titrant used recorded. Two blanks may then be prepared by repeating the previously described procedure without adding the prepolymer sample to the flask. The amount of ethylene diamine (ED) required for chain extension may then be calculated by using the equations shown below.

NCO Content (moles NCO/gram of solids =

$$\frac{2(\text{ml titrant for blank} - \text{ml titrant for sample})}{\text{sample weight (1,000)}}$$

Moles of NCO in Reactor =

(NCO Content) (gram solids in reactor)

$$\% \text{ ED} = \frac{\text{moles NCO in reactor}}{2 \text{ (moles Theoretical ED)}} \times 100$$

Grams of ED =

$$\frac{(\text{Actual \% ED added})(\text{Moles of Theoretical ED}) (60.1)}{(100)}$$

In addition, the following two steps may be performed simultaneously with the titration.

Chain extension may be attained by adding a solution containing about 40 to 60 wt %, and preferably about 50 wt %, of the theoretical amount of ethylene diamine (ED) in a solvent such as dimethyl formamide (DMF), in a proportion of ED:DMF of about 1:5. The ED solution may be added to the mixture over a period of, e.g., about 30–45 minutes. In general, about 20 minutes is sufficient to permit complete reaction. Half the remaining ED, as calculated below, may be added at this point.

Remaining ED (%) = Titrated ED % − ED % added

After the addition of the ED, e.g., the reaction may go to completion in about 20 minutes. The above-described titration/calculation may then be repeated until the presence of isocyanate is no longer detected by titration. If isocyanate is still present after all the ED/DMF solution is added and reacted, the reaction may be aborted and discarded. If no isocyanate is detected, the mixture may be further stirred for, e.g., about 30 minutes, at about 15° C. with a variance of about 2° C. The polymer may then be stabilized by the addition of about 0.5% to 5% Tinuvin 328 and 0.5% to 5% Tinuvin 770, and preferably 0.5 to 1% of each, based on total solids of the polyurethane polymer formed. This may be attained with about 25 wt % solution of Tinuvin 328 and Tinuvin 770 in THF.

Tinuvin 770 is a commercially available product comprising bis(2,2,6,6-tetramenthyl-4-piperidyl)sebacate or bis(2,2,6,6-tetramethyl-4-piperidinyl)decanedioate. Similarly, Tinuvin 328 is one of a family of substituted benzotriazoles. Other families of compounds may also be used in their stead. Examples of stabilizers are antioxidants, thermal stabilizers and ultraviolet (UV) light absorbers include, but are not limited to, hindered amine light stabilizers, sterically hindered phenol compounds, compounds with sterically hindered phenolic hydroxyl groups, compounds from the hydroxyphenyl-benzotriazole family, and light stabilizers of the benzophenone-type. Combinations of any or all of the compounds listed above may also be used as well as other stabilizers known in the field.

The reaction mixture may then be further stirred for, e.g., about 30 minutes at about 15° C. with a variance of about 2° C., and the thus attained polyurethane filtered through, e.g., a woven stainless steel 10 micron filter into, e.g., clean, dry glass containers.

Of particular importance are the temperature ranges and the ratio or proportion of the reactants in the different reaction steps. The optimal reaction temperature for the reaction of aromatic diisocyanates with polyols is about 50° to 60° C. The optimal reaction temperature for the reaction of aliphatic diisocyanates with polyols is about 100° to 110° C. The optimal reaction temperature for amine terminated reactants is about 0° C. and 25° C. This reaction temperature applies to amines used as chain extenders and amines used in the soft segment. The diisocyanate and all reactants which contribute an active hydrogen, i.e., polyols, diamines, amines, may be added in a proportion of about 0.9 to 1.2 and more preferably about 0.95 to 1.1. The reactants may be added to a solvent as described above.

These reactions are typically conducted at atmospheric pressure, but it may also be undertaken at other pressures such as in the range of about 0.1 to 100 atm.

Although the copolymer of the invention may be prepared in a wide range of molecular weights, for some applications preferred is a molecular weight of about 5,000 to 1,000,000, and more preferable about 6,000 to 60,000. Still another range of preferred copolymer molecular weight is about 2,000 to 10,000, and more preferable about 3,000 to 6,000. Some of these may be used as pre-polymers capable of further reaction during fabrication, whereas higher molecular weight homologues are utilized as the final polymers for preparation of the films such as membranes, sheets or hollow fibers.

The soft segment used in the preparation of the polyurethane of the invention may be a polyfunctional aliphatic polyol, or a polyfunctional aliphatic or aromatic amine such as are commonly used for the preparation of polyurethanes or mixtures thereof. The molecular weight of the soft segment is typically about 200 to 1,000,000, and preferably about 400 to 9,000.

The aliphatic polyols of the soft segment may be selected from the group consisting of linear and branched polyalkylene and polyalkenyl oxides, random and block copolymers thereof, polycarbonate polyols, hydroxyl-terminated silicones, random and block copolymers thereof with polyalkylene oxides, linear and branched polyalkenyl and polyalkylene polyols, and mixtures thereof. However, other polyols may also be utilized if the resultant polymer posses the required water absorptivity.

Examples of polyols that are suitable for use in the present invention are polyethylene oxides, polypropyleneoxides, polytetramethylene oxides, random or block polypropylene oxide-polyethylene oxide copolymers, various ethyleneoxide-terminated polyols, random or block polytetramethylene oxide-polyethylene oxide copolymers, polycarbonate diols and triols, multifunctional hydroxyalkyl- or amine-terminated silicones, random or block silicone-polyethyleneoxide copolymers, polybutadiene diols and triols, polyisobutylene diols and triols, and mixtures thereof.

The amines of the soft segment may be selected from the group consisting of amine-terminated homologues of the exemplary polyols, including but not limited to polyamine-terminated alkylene oxides and random and block copolymers thereof, polyamine-terminated silicones, random and block copolymers thereof with polyalkylene oxides and mixtures thereof.

Examples of the amines that are suitable for use in the present invention are multifunctional amine-terminated polytetramethylene oxides, multifunctional amine terminated polyethylene oxides, random or block multifunctional amine terminated polypropylene oxide-polyethylene oxide copolymers, random or block multifunctional amine-terminated polytetramethylene oxide-polyethylene oxide copolymers, multifunctional amine-terminated silicones, random or block amine-terminated silicon polyethylene oxide copolymers and mixtures thereof.

Suitable polyisocyanates for the preparation of the hard segment of the copolymer of the invention are aromatic or aliphatic polyisocyanates.

The organic diisocyanates may be selected from the group consisting of alkyl diisocyanates, arylalkyl diisocyanates, cycloalkylalkyl diisocyanates, alkylaryl diisocyanates, cycloalkyl diisocyanates, aryl diisocyanates, cycloalkylaryl diisocyanates, all of which may be further substituted with oxygen, and mixtures thereof.

Examples of polyisocyanates are 4,4'-diphenylmethane diisocyanate, hexamethylene diisocyanate, dicyclohexylmethane diisocyanate, 2,4-toluene diisocyanate, 2,6-toluene diisocyanate, hexamethylene-1,6-diisocyanate, tetramethylene-1,4-diisocyanate, cyclohexane-1,4-diisocyanate, naphthalene-1,5-diisocyanate, diphenylmethane-4,4'-diisocyanate, xylylene diisocyanate, dicyclohexylmethane-4,4'-diisocyanate, 1,4-benzene diisocyanate, 3,3'-dimethoxy-4,4'-diphenyl diisocyanate, m-phenylene diisocyanate, isophorone diisocyanate, polymethylene polyphenyl diisocyanate, 4,4'-biphenylene diisocyanate, 4-isocyanatocyclohexyl-4'-isocyanatate, and mixtures thereof. Preferred are diphenylmethane diisocyanate, dicyclohexylmethane diisocyanate and mixtures thereof.

The chain extender of the hard segment used in the preparation of the copolymers of the invention may be an aliphatic polyol or an aliphatic or aromatic polyamine such as those known for preparing polyurethanes.

The polyol for the hard segment may be preferably selected from the group consisting of alkylene, cycloalkylene and arylene diols, triols, tetraalcohols, and pentaalcohols, and mixtures thereof.

Examples of polyols suitable for the preparation of the hard segment are 1,4-butanediol, ethylene glycol, 1,6-hexanediol, glycerine, trimethylolpropane, pentaerythritol, 1,4-cyclohexane dimethanol, phenyl diethanolamine, and mixtures thereof, among others. However, other polyols are also suitable.

The polyamine of the hard segment may be selected from the group consisting of alkyl, cycloalkyl and aryl amines which may be further substituted with N, O, or halogen, complexes thereof with alkali metal salts, and mixtures thereof.

Suitable polyamines for preparing the hard segment are p,p'-methylene dianiline and complexes thereof with alkali metal chlorides, bromides, iodides, nitrites and nitrates, 4,4'-methylene-bis(2-chloroaniline), piperazine, 2-methylpiperazine, oxydianiline, hydrazine, ethylenediamine, hexamethylenediamine, xylylenediamine, bis(p-aminocyclohexyl)methane, dimethyl ester of 4,4'-methylenedianthranilic acid, p-phenylenediamine, m-phenylenediamine, 4,4'-methylene bis(2-methoxyaniline), 4,4'-methylene bis(N-methylaniline), 2,4-toluenediamine, 2,6-toluenediamine, benzidine, dichlorobenzidine, 3,3'-dimethylbenzidine, 3,3'-dimethoxybenzidine, diansidine, 1,3-propanediol bis(p-aminobenzoate), isophorone diamine, and mixtures thereof.

In another embodiment, the hard segment of the copolymer may further comprise an end group selected from the group consisting of monofunctional aliphatic alcohols, polyols, aliphatic or aromatic amines and mixtures thereof. Preferred monofunctional aliphatic polyols for the end group are monofunctional polyalkylene oxides, siloxanes, and mixtures or copolymers thereof. Examples of aliphatic polyols are monofunctional polyethylene oxides, monofunctional polytetramethylene oxides, monofunctional polypropylene oxides, monofunctional siloxanes, and mixtures and/or copolymers thereof. However, others are also suitable.

The monofunctional amines of the end group may be selected from the group consisting of dialkylamines, amine-functional siloxanes, amine-terminated polyalkylene oxides and mixtures and copolymers thereof.

The hard segment of the copolymer of the invention may preferably have a molecular weight of about 160 to 10,000, and more preferably about 200 to 2,000. Its components also have preferred molecular weights as shown in Table 11 below.

TABLE 11

| Preferred Molecular Weights for Hard Segment Component | | |
|---|---|---|
| Hard Segment Component | Most Preferred MW | Preferred MW |
| Aromatic Diisocyanates | 150–270 | 100–500 |
| Aliphatic Diisocyanates | 150–270 | 100–500 |
| Chain Extenders | 60–200 | 18–500 |

Although both the hard and soft segments may be utilized in a broad range of molecular weights, Table 12 below shows typical useful molecular weight ranges and preferred molecular weight ranges for some exemplary components of the soft segment.

TABLE 12

Preferred Molecular Weights for Soft Segment Components

| Soft Segment Component | Most Preferred MW | Preferred MW |
| --- | --- | --- |
| Polyethylene oxide | 1000–9,000 | 200–1,000,000 |
| Polytetramethylene oxide | 1000–9,000 | 500–50,000 |
| Polypropylene oxide-polyethylene oxides | 1000–5,000 | 500–50,000 |
| Polytetramethylene oxide-polyethylene oxides | 1000–2,000 | 500–50,000 |
| Amine-capped polypropylene-polyethylene oxides | 600–6,000 | 200–1,000,000 |
| Polycarbonates | 300–3,000 | 200–50,000 |
| Amine-capped polytetramethylene oxides | 500–2,000 | 200–50,000 |
| Hydroxyl-alkyl and amine-capped silicones | 200–5,000 | 100–20,000 |
| Silicone-polyethylene oxides | 500–5,000 | 200–1,000,000 |
| Polybutadienes | 500–3,000 | 200–50,000 |
| Polyisobutylenes | 1,000–5,000 | 500–10,000 |

The content of hard segment of the copolymer is typically about 5 to 45 wt %, the remainder of the polymer consisting of soft segment, which may be a combination of hydrophilic, hydrophobic and amphipathic oligomers.

In one preferred embodiment, the copolymer comprises about 9 to 30 wt % of the hard segment, and more preferably 10 to 28 wt % thereof. Similarly, a typical content of the soft segment is about 91 to 70 wt %, and more preferably about 90 to 72 wt %. However, other proportions of hard and soft segments are also suitable for practicing this invention.

A polymer made from this composition will have the properties described in Table 13 below.

TABLE 13

Characteristics of Film of the Invention

| Characteristics | Range |
| --- | --- |
| Tensile strength | > about 350 and up to about 10,000 psi |
| Elongation at Break | > about 300% and up to about 1,500% |
| Water Absorption + Hydrophilic Soft Segment | > about 100% and up to about 2,000% dry wt |
| or more preferably | > about 50% and up to about 95% wet wt |
| Water absorption only | > about 100% and up to about 2000% dry weight |
|  | > about 50% and up about 95% wet wt |
| Thickness (when unsupported) | about 5 to 100 microns |
| Thickness (when supported or reinforced) | about 1 to 100 microns |

This invention also provides a non-porous, semipermeable, biocompatible film that comprises the block copolymer of the invention. In a preferred embodiment, the film is formed from the copolymer of this invention. In another preferred embodiment the film is coated onto a support. In still another preferred embodiment, the film is an integrated part of the substrate and is made of the same or similar polymer.

In particularly preferred embodiments, the non-porous film of the invention is provided in the form of a flexible sheet and a hollow membrane or fiber. Typically, the flexible sheet may be prepared as a long rollable sheet of about 10 to 15 inches width and 1 to 6 feet length. However, other dimensions may also be selected. Of particular importance is the thickness of the sheet which may be about 5 to 100 microns, and more preferably about 19 to 25 microns when it is to be used without support or reinforcement.

The flexible sheet is prepared from the block copolymer of the invention by methods known in the art, typically, by casting, and more preferably by casting on a web or release liner. As already indicated, the composition may be coated as a film onto a substrate. Where permanently supported on a reinforcing web, e.g., a fabric, the film or membrane may be thinner, e.g., as thin as about 1 micron, whereas when used unsupported the thickness may only be as low as about 5 to 10 microns.

When membranes are fabricated from the polymer of the invention by knife-over-roll casting onto a release paper, web or liner in the form of dry films, they may have an about 1 to 100 micron nominal thicknesses on a continuous coating line. A 20-foot-long continuous web coater may be utilized having, e.g., a maximum web width of 15 inches equipped with two forced-air ovens. In one particular embodiment, the coater may be modified for clean operation by fitting the air inlet ducts with High Efficiency Particulate Air (HEPA) filters. A nitrogen-purged coater box may be used to hold and dispense filtered polymer solutions or reactive prepolymer liquids. However, other set-ups are also suitable.

All but trace amounts of a casting solvent, e.g., dimenthylformamide may be removed by coater's hot air ovens fitted with HEPA filters. After membrane casting, membrane and substrate may be further dried to reduce residual solvent content to less than about 100 ppm, as determined by liquid chromatography. The thickness of the fully-dried cast films may be measured by, e.g., using a spring micrometer sensitive to 0.0001 inch (2.5 $\mu$M) or visually by using a microscope.

The membrane of this invention may have any shape resulting from a process utilizing a liquid which is subsequently converted to a solid during or after fabrication, e.g., solutions, dispersions, 100% solids prepolymer liquids, polymer melts, etc. Converted shapes may also be further modified using methods such as die cutting, heat sealing, solvent or adhesive bonding or any of a variety of other commonly-used fabrication methods. For example, when in the form of a hollow tube, the membrane is generally prepared with a diameter of about 0.5 to 10 mm, and more preferably about 1 to 3 mm, and a thickness of about 1 to 100 microns, and more preferably about 19 to 25 microns. The hollow membrane may easily be prepared in long rollable form, and be cut to a length of about 0.75 to 31 inches, and more preferably about 0.5 to 6 inches.

Hollow fibers may be fabricated from the polymer solutions by dipping clean, dry, mandrels, e.g., a 1 mm diameter stainless steel mandrel into the polymer solution. The mandrel may be suspended in a baffled chamber maintained at above normal room temperature, e.g., about 27° to 50° C., in a Class 1,000 Cleanroom. The mandrel may be attached to a motor driven cable and dipped into the polymer solution and withdrawn at an even speed and the solvent may be allowed to evaporate. The mandrel may then be inverted, hung and dipped again. This procedure may be repeated, e.g., three times, to yield a tube with a single wall thickness of, e.g., 19 microns. Multiple dippings may be performed to reduce the chances of pinholes occurring in the polymer hollow fibers. The mandrels may then be left in the heated chamber for at least 16 hours to allow the solvent to evaporate. To aid in the removal of the hollow fibers from the mandrel, the coated mandrel may be soaked in distilled water for, e.g., one hour. The removal of any remaining residual solvent may be achieved by water extracting the hollow fibers in distilled water for, e.g., 24 hours. The hollow fibers may then be flushed three times with distilled water and packaged in distilled water in clean glass tubes. Prior to filling the hollow fibers they may be leak-tested. One end of the hollow fiber may be heat-sealed, the fiber filled with distilled water and the remaining end heat-sealed. The filled hollow fiber may then be pressurized and the tube examined for water leakage under pressure.

The fabrication methods just described employ liquid solutions or reactive liquid prepolymers of the membrane polymers. In the case of essentially linear polymers of the present invention, thermoplastic fabrication methods may also be employed. Membrane polymers made by the bulk or solvent-free polymerization method described above may be cast into, e.g., a teflon-lined pan during the polymerization reaction. As the reaction proceeds and the polymerizing liquid becomes a rubbery solid, the pan may be postcured in an oven at, e.g., 100°-120° C. for about 1 hour. Upon cooling, the rubbery mass may be chopped into pellets and dried in a dehumidifying hopper dryer for, e.g., about 16 hours. The dry pellets may then be compression molded, e.g., at about 175° C. to form a flat membrane which, when cool, will leave a thickness of about 50 $\mu$M. Extrusion, injection molding, calendering and other conversion methods that are well-known in the art may also be used to form membranes, films and coatings of the polymers of the present invention, including hollow fibers.

As already indicated above, the non-porous film of the invention is substantially permeable to molecules of molecular weight of up to about 6,000 to 600,000, and more preferably of up to about 6,000 to 60,000, and is substantially impermeable to molecules of molecular weight greater than about 6,000 to 600,000 daltons, and more preferably greater than about 100,000. The utility of a specific membrane is based on its ability to allow the permeation of desired permeants while preventing the permeation of other permeants, including all condensed phases of matter. It is within the scope of the present invention to provide membranes with permeability to permeants of up to about 600,000 daltons and higher, while simultaneously excluding permeants of higher molecular weight and/or lower solubility. To control the permeability rate and/or MW cut-off based on permeant solubility in the water-swollen membrane polymer, the soft segment composition, content and molecular weight may be varied during polymer synthesis.

Commercially-available polyether oligomer, for example, may be obtained in molecular weights ranging from a few hundred to a few thousand. To achieve molecular weight cutoffs higher than those obtainable with commercially-available soft segment oligomers, available soft segment oligomers may be coupled together prior to the synthetic reaction to obtain the final membrane polymer.

In polyurethane synthesis, a so-called three-step reaction may be employed, in which the first step involves covalently bonding two or more oligomers together, while optionally retaining the oligomer's original end-groups by appropriate control of the stoichiometry of the coupling reaction. For example, three moles of hydroxyl-terminated polyether oligomer might be reacted with two moles of a diisocyanate optionally chosen to be different from the isocyanate used in the hard segment of the final polymer. Using a different diisocyanate to couple soft segment oligomers minimizes the association of the coupling segment with the hard segment of the polymer, which is desireable for maximum permeability. For instance, if the original polyol molecular weight were about 2,000, the coupled oligomer would have an average molecular weight of about 6,000 plus the molecular weight of the two diisocyanates used in the urethane-forming coupling reaction. When this coupled oligomer is subsequently reacted to form the final membrane polymer, the maximum end-to-end distance between hard segments is increased more than three times, relative to the original 2,000 molecular weight oligomer before coupling. When an organic diisocyanate is used to couple soft segments, and that diisocyante is chosen to be different from the diisocyanate used in the hard segment, the coupling diisocyanate is considered to be part of the soft segment.

Preferred are low hard segment lengths of molecular weights, e.g., about 160 to 1,000, and a proportion of hard to soft segment of about 1 to 11, and more preferably about 1 to 6.

The above disclosure sets forth a number of embodiments of the present invention. Other arrangements or embodiments, not necessarily set forth in detail herein, may be practiced under the general teachings of the present invention, and as set forth in the following examples, which are not intended to be limiting in nature.

EXAMPLES

Example 1

One Step Synthesis 64 grams of a polyethylene oxide, molecular weight about 3,350, were mixed with 8 g butanediol in a disposable beaker at 60° C. To this were added, with vigorous stirring, 28 g diphenylmethane diisocyanate (MDI). When all reactants were homogeneous a drop of catalyst, stannous octoate or dibutyltin dilaurate, was added. The mixture was poured into a pan and postcured for 45 to 60 minutes in a 100° C. oven. This reaction may also be performed in an extruder to yield a product in pelletized form. The results are summarized in Table 14 below.

TABLE 14

| Hydrophilic Urethane: One-Step Synthesis With Stoichiometric Imbalance For MW Control | | |
|---|---|---|
| Hydrophilic PU | solid polymer (wt %) | mole equivalents (100 g batch) |
| MDI | 28.00 | 0.2238 |
| Butanediol | 8.00 | 0.1776 |
| Carbowax 3350 | 64.00 | 0.0382 |
| Total | 100.00 | |
| % HS | 36.00 | |
| % SS | 64.00 | |
| Mole NCO | | 0.2238 |
| Mole Active H | | 0.2158 |

TABLE 14-continued

Hydrophilic Urethane: One-Step Synthesis
With Stoichiometric Imbalance For MW Control

| Hydrophilic PU | solid polymer (wt %) | mole equivalents (100 g batch) |
|---|---|---|
| Ratio NCO:H | | 1.04 |

Example 2

Two-Step Synthesis 72.15 g of a blend of 15 wt % polyethylene oxide, molecular weight about 1,450, and 85 wt % polypropylene oxide-polyethylene oxide copolymer, molecular weight about 2,000, were blended with 1.25 g dibutylamine at 500° C. in a glass reaction vessel. This blend was dissolved in 80.0 g dimethylformamide and 24.0 g diphenylmethane diisocyanate were then added with vigorous stirring. The reaction was continued for about 3 hours at 50°±5° C. The thus obtained product was dissolved in 220 g of dimethylformamide, and the resulting solution cooled to 10° C. in an ice bath. 2.6 g ethylenediamine dissolved in 100 g of dimethylformamide were added to the cold solution with vigorous stirring, and the stirring was continued for about 30 minutes. The polyurethaneurea solution was then removed from the reaction vessel and filtered through an 8–9 micron stainless steel filter. The results obtained from three separate experiments are summarized in Tables 15, 16, and 17 below.

TABLE 15

Hydrophilic Urethane Preparation: Two-Step Synthesis Monofunctional Amine-Terminated PEO End Group For MW Control

| Hydrophilic PU | solid polymer (wt %) | mole equivalents (100 g batch) |
|---|---|---|
| MDI | 24.14 | 0.1929 |
| ED | 2.85 | 0.0948 |
| Witco EPD-56 | 11.50 | 0.0117 |
| Carbowax 1450 | 61.51 | 0.0865 |
| Total | 100 | |
| % HS | 26.99 | |
| % SS | 73.01 | |
| Mole NCO | | 0.1929 |
| Mole Active H | | 0.1930 |
| Ratio NCO:H | | 0.9998 |

TABLE 16

Hydrophilic Urethane Preparation: Two-Step Synthesis

| Hydrophilic PU | solid polymer (wt %) | mole equivalents (100 g batch) |
|---|---|---|
| MDI | 18.90 | 0.1510 |
| ED | 1.35 | 0.0449 |
| Witco EPD-56 | 10.00 | 0.0101 |
| BASF ER1250/25 | 14.75 | 0.0227 |
| Carbowax 1450 | 51.30 | 0.0721 |
| Jeffamine M-2070 | 3.70 | 0.0019 |
| % HS | 23.95 | |
| % SS | 76.05 | |
| Mole NCO | | 0.1510 |
| Mole Active H | | 0.1517 |
| Ratio NCO:H | | 0.9958 |

TABLE 17

Hydrophilic Urethane Preparation:
Two-Step Synthesis With Dialkylamine
End Group for MW Control

| Hydrophilic PU | solid polymer (wt %) | mole equivalents (100 g batch) |
|---|---|---|
| MDI | 24.00 | 0.1918 |
| ED | 2.60 | 0.0865 |
| Witco EPD-56 | 10.95 | 0.0111 |
| Carbowax 1450 | 61.20 | 0.0860 |
| Dibutylamine | 1.25 | 0.0097 |
| % HS | 27.85 | |
| % SS | 72.15 | |
| Mole NCO | | 0.1918 |
| Mole Active H | | 0.1933 |
| Ratio NCO:H | | 0.9922 |

Example 3

Three-Step Synthesis 69.89 g polyethylene oxide, molecular weight about 1,450, were reacted for 3–4 hours with 8.18 g dicyclohexylmethane diisocyanate at 100° C. in a glass reaction vessel. The product was cooled to 50° C. and 80 g dimethylformamide and 1.24 g dibutylamine were added. 18.47 g diphenylmethane diisocyanate were added to this with vigorous stirring, and the reaction continued for 3 hours at 50°±5° C., with stirring. The thus obtained product was dissolved in 220 g dimethylformamide, and the resulting solution cooled to 10° C. in an ice bath. 3.21 g ethylenediamine dissolved in 100 g of dimethylformamide was added to the cold solution, with vigorous stirring, and the stirring continued for 30 minutes. The polyurethaneurea solution was then removed from the reaction vessel and filtered through an 8–9 micron stainless steel filter. The results are shown in Table 18 below.

TABLE 18

Hydrophilic Urethane Preparation:
Three-Step Synthesis

| Hydrophilic PU | solid polymer (wt %) | mole equivalents (100 g batch) |
|---|---|---|
| Prepolymer Step | | |
| HMDI | 10.76 | 0.0763 |
| Carbowax 1450 | 89.24 | 0.1117 |
| Polymer Formation | | |
| MDI | 18.47 | 0.1476 |
| ED | 3.21 | 0.1068 |
| 1st step prepolymer | 77.08 | 0.0312 |
| Dibutylamine | 1.24 | 0.0096 |
| Total | 100 | |
| % HS | 22.92 | |
| % SS | 77.08 | |
| Mole NCO | | 0.1476 |
| Mole Active H | | 0.1486 |
| Ratio NCO:H | | 0.9931 |

Example 4

Two-Step Polymer Synthesis

The purity, molecular weight and water content of the starting materials were determined by titration. The polyurethanes were synthesized in glass batch reactors with glass-distilled solvents using a two-step prepolymer/chain extension method as described in Example 2.

The film forming polymer used was a polyurethaneurea with a diphenylmethanediisocyanate/ethylene diamine hard segment and a hydrophobic and hydrophilic mixed polyalkyleneoxides soft segment. A series of five elastomers with nominal hydrophilic contents of 0, 10, 20, 30, 40 and 50 wt % were synthesized by the two step, prepolymer/chain extension method described in Example 2 in dimethylformamide (DMF) solvent. The optimum molecular weight of each polyol was determined to be about 1,400 and 2,000 and then fixed for the whole series of polymers, subject to availability from commercial suppliers. Infrared spectrophotometry and/or titration were used to monitor the disappearance of isocyanate to assure the completion of the reaction. The content of the hard segment was held constant at about 20 wt % for a series of polymers. The membrane casting solution of each polymer was filtered through a 10 micron 316 woven stainless steel filter and outgassed under mild vacuum prior to film casting.

Example 5

Preparation of Membranes by Knife Over Roll Casting

Membranes were fabricated from the polymers of the above examples by knife-over-roll casting onto a release paper, web or liner in the form of dry films of 1 to 100 micron nominal thicknesses on a coating line. A 20-foot-long continuous web coater was utilized, that had a maximum web width of 15 inches and was equipped with two forced-air ovens. A nitrogen-purged coater box was used to hold and dispense filtered polyurethane solutions.

All but trace amounts of a casting solvent, such as dimenthylformamide, were removed by the coater's hot air ovens which were fitted with HEPA filters. After membrane casting, membrane and substrate were further dried to reduce residual solvent content to about 100 ppm, as determined by liquid chromatography. The thickness of the fully-dried cast films were measured using either a spring micrometer sensitive to 2.5 microns or visually using a microscope.

Example 6

Selective Permeation of Glucose

A 1 wt % glucose solution was prepared in phosphate buffered saline (PBS). In the glucose experiments for all of the polymer films, eight permeation chambers with similar membranes were used. The experiment was repeated utilizing membranes of increasing hydrophilicity, between 0% and 85%. As the hydrophilicity is increased, the permeability of the membrane increases while the permeation time decreases. The glucose concentration on the downstream side of each chamber was determined using a quantitative glucose oxidase enzymatic assay. The test sample was added to a mixture containing glucose oxidase, peroxidase and o-dianisidine. The reaction was allowed to proceed to completion, for approximately 45 minutes at 23° C. The final color intensity was measured at 450 nm on a Milton Roy Visible Spectrophotometer, Model Spectronic 20D, and found to be proportional to the glucose concentration. A calibration curve was generated by plotting the glucose concentrations from 0 to 3000 µg/ml (0 to 3 mg/ml) vs. the absorbance at 450 nm. The data were analyzed using linear regression to generate the line with the best fit. This correlation was used to calculate the glucose concentration in the unknown samples.

A model was developed using Mathematica ® to calculate the permeability coefficient, p, for each cell. The permeabilities were then averaged. The % equilibrium for each cell was calculated. FIG. 1 of this patent contains these data for membranes of increasing hydrophilicity. The curves of FIG. 1 were generated using the averaged data from two chambers for each point. The first seven polymers in this series (i.e., 0 to 66% hydrophilicity inclusive) comprised a nominal soft segment molecular weight of 1,700 daltons. The polymer with 85% hydrophilicity had an 8,000 dalton soft segment molecular weight and a glucose permeability of 29,000. After correcting for its higher hydrophilicity using a linear extrapolation, its glucose permeability is 240% higher than the homologous polymer with a nominal 1,750 soft segment molecular weight. This demonstrates the ability to increase permeability by increasing soft segment molecular weight of the polymers of the present invention. Using the mathematical model developed, a best fit regression curve was generated. The p calculated from the regression analysis is reported herein. Thus, the fast permeability of the membranes for the glucose molecule was demonstrated to be increased at increasing degrees of hydrophilicity.

Example 7

Tensile Properties of the Membranes of the Invention

The mechanical properties in tension of the polymers prepared in Example 4 were determined according to ASTM procedure D1708. A Lloyd Universal Testing Machine, Model 500N, and a 112 pound load cell was used to evaluate the polymers. The initial modulus, tensile strength at break, and the ultimate elongation were calculated for water-extracted, solvent-cast films. The films were equilibrated at 23° C. and 50% relative humidity for 24 hours prior to testing. Microdogbone samples of both dry and hydrated films were used to determine the tensile properties at 23° C. for each polyurethaneurea. The hydrated samples were prepared by placing the films in water for 24 hours, die cutting the samples and returning them to the water. Die cutting the samples after they were hydrated insured that the width of all the microdogbones was the same regardless of the amount of swelling that occurred for each polymer. The samples were removed from the water, the thickness was measured and they were tested. Five test specimens of each polymer, dry and hydrated, were analyzed. The instrument is interfaced to an IBM compatible computer which programs the machine and performs the appropriate calculations and the statistical data reduction. The tensile porperties of membranes according to this invention having increasing hydrophilicity are provided in Table 19 below.

TABLE 19

Tensile Properties of Dry and Hydrated Polyurethaneureas as a Function of Membrane Hydrophilicity

| Hydrophilic Content | Initial Modulus (psi) | Tensile Strength (psi) | Ultimate Elongation (%) |
|---|---|---|---|
| 0% | | | |
| dry | 827 ± 46 | 6025 ± 304 | 945 ± 41 |
| hydrated | 1059 ± 87 | 5076 ± 236 | 936 ± 24 |
| 10% | | | |
| dry | 722 ± 32 | 5783 ± 514 | 994 ± 44 |
| hydrated | 955 ± 25 | 3942 ± 132 | 945 ± 22 |
| 20% | | | |
| dry | 737 ± 75 | 4428 ± 405 | 1039 ± 67 |
| hydrated | 895 ± 25 | 3171 ± 237 | 1026 ± 61 |
| 30% | | | |
| dry | 681 ± 89 | 3409 ± 324 | 1110 ± 59 |
| hydrated | 677 ± 104 | 2560 ± 190 | 994 ± 68 |
| 40% | | | |
| dry | 740 ± 69 | 1325 ± 85 | 774 ± 18 |
| hydrated | 555 ± 96 | 1075 ± 45 | 630 ± 23 |

TABLE 19-continued

Tensile Properties of Dry and Hydrated Polyurethaneureas as a Function of Membrane Hydrophilicity

| Hydrophilic Content | Initial Modulus (psi) | Tensile Strength (psi) | Ultimate Elongation (%) |
|---|---|---|---|
| 50% | | | |
| dry | 598 ± 63 | 1100 ± 98 | 830 ± 29 |
| hydrated | 456 ± 79 | 817 ± 44 | 593 ± 30 |

Example 8

Water Absorption and Extractables

Since the equilibrium water uptake is an important determinant of the moisture vapor transmission rate and the protein permeability of a polymer, the amount of water absorbed and the amount of material extracted from the polyurethaneureas were determined as well. An A&D analytical balance, Model FR-200, was used to accurately weigh samples to 0.1 mg which had been equilibrated for 24 hours at equilibrated at 23° C. and 50% relative humidity prior to testing. Three test specimens of each polymer were placed in distilled water at 23° C. and 37° C. After twenty four hours of water immersion the samples were removed, blotted dry and weighed. They were then dried for 24 hours at 23° C. and 50% relative humidity and reweighed. The weight percent of water in the polymer, or water absorption on a wet basis, which is always ≦100, was calculated with the following equation.

$$\frac{Sw - Fw}{Sw} \times 100$$

Swelling related to the dry state is usually referred to as hydration or water absorption on a dry basis. Thus, the percent hydration or water regain, which may be greater than 100, was calculated from the following mathematical equation.

$$\frac{Sw - Fw}{Fw} \times 100$$

The degree of swelling, which is greater than or equal to about 1.0, was calculated as the following ratio.

$$\frac{Sw}{Fw}$$

Similarly, the percentage of extractables was calculated as follows.

$$\frac{Fw - Ow}{Ow} \times 100$$

For all the above formulas, the variables used represent the following parameters.

Ow = original dry weight (grams)
Sw = swollen wet weight (grams)
Fw = final dry weight (grams)

The results obtained for membranes of increasing hydrophilities are shown in Table 20 below.

TABLE 20

Water Absorption and Extractables at 23° C. and 37° C. as a Function of Membrane Hydrophilicity

| Hydrophilic Content (%) | Dry Basis H$_2$O Absorbed (%) | | Weight Basis H$_2$O Absorbed (%) | | Extractables (%) | |
|---|---|---|---|---|---|---|
| | 23° C. | 37° C. | 23° C. | 37° C. | 23° C. | 37° C. |
| 0 | 1.3 | 1.6 | 1.3 | 1.6 | 0.1 | 0.3 |
| 10 | 8.0 | 6.9 | 7.4 | 6.5 | 0.1 | 0.3 |
| 20 | 21.7 | 16.2 | 17.9 | 14.0 | 0.1 | 0.3 |
| 30 | 36.1 | 31.2 | 26.5 | 23.8 | 0.3 | 0.5 |
| 40 | 63.2 | 48.4 | 38.7 | 32.6 | 0.6 | 0.7 |
| 50 | 78.4 | 65.3 | 43.9 | 39.5 | 0.7 | 0.9 |

Example 9

Permeation of Molecules of Varying Molecular Weights

Diffusion experiments were conducted in which the heat-sealed, hollow-fiber membranes of this invention prepared as in Example 11 below were filled with permeant solutions containing an $^{125}$I-labeled tracer molecules of various molecular weights and placed in a test tube filled with permeant-free solution and incubated at 37° C. Aliquots were withdrawn from the test tube and measured in a well counter. Using as the membrane thickness 19 microns, and as an area of the membrane 0.016 cm$^2$, the measured volumes of the hollow fiber and test tube, and the starting concentrations inside and outside the hollow fiber, the permeability coefficient, p, was calculated from each sample.

Regression analysis was used to calculate the best fit value for p, in this and in the diffusion cell experiments. The permeability coefficient P may be expressed in different units by applying suitable conversion factors. Data obtained for various proteins are shown in Table 21 below.

TABLE 21

| Permeability Coefficients for Proteins of Varying MWs | | |
|---|---|---|
| Protein | Molecular Weight | p (μg · cm/cm$^2$ · day · g/cm$^3$) |
| Glucose | 180 | 9620 |
| Angiotensin I | 1440 | 90 |
| Glucagon | 3550 | 400 |
| Insulin | 6000 | 2300 |
| Aprotinin | 6500 | 25 |
| Albumin | 68000 | 10 |
| IgG | 158000 | 0 |

Thus, it was shown that while glucose has a high p, molecules of increasing MW have lower p's. Since the dense membranes of the present invention have permeabilities which are determined by the solubility of the permeants as well as their diffusivity, the permeability coefficients do not vary strictly with molecular weight (size) of the permeants.

Example 10

Oxygen Permeability of the Membranes of this Invention

The oxygen permeability was determined for various membranes prepared with the polymers of this invention using a Createch 201 T Permeometer and a Rehder flat polargraphic cell in a 100% humidity chamber at 35°±0.2° C. For each material reading four 13 mm circles of material were stacked together on the electrode. All materials were fully hydrated in 0.9% saline and incubated at 35° C. prior to readings being taken. The readings for three different samples of each material were averaged to produce the average reading in micro amps. The central thickness of each sample was measured with a micrometer. The central thickness of each material were averaged to produce the average thickness in cm. The results of the experiment are shown in Table 22 below.

TABLE 22

Oxygen Permeability Through Hydrophilic and Hydrophobic Polymers

| Example (Hydrophilic Content %) | Water Abs. (%) Dry Basis | Water Abs. (%) Dry Basis | Dk/L ($10^{-9}$ cc/cm$^2$ sec mm Hg) | Dk ($10^{-11}$ cc cm/cm$^2$ sec mm Hg) |
|---|---|---|---|---|
| A (0) | 0 | 0 | 1.85 | 32.8 |
| B (9) | 4 | 4 | 5.4 | 12.4 |
| C (24) | 20 | 17 | 5.90 | 10.5 |
| D (28) | 22 | 18 | 5.37 | 14.0 |
| E (34) | 35 | 26 | 5.48 | 15.4 |
| F (58) | 100 | 50 | 8.80 | 44.7 |
| G (66) | 92 | 48 | 9.25 | 12.0 |

Example A is a polymer made from the reaction of MDI with and amine-terminated siloxane. Examples B through F are polymers made from reacting MDI with a hydrophilic/hydrophobic soft segment and then chain extending with ED. The ratio of hydrophilic to hydrophobic content in the soft segment was varied, with Example B being the most hydrophobic and Example F the most hydrophilic. Example G has a MDI/ED hard segment, a mixed hydrophobic/hydrophilic soft segment and was chain terminated with dibutylamine.

Example 11
Preparation of Hollow Fibers

Hollow fibers of 1 mm nominal diameter and 19 micron thickness assessed by diffusion studies were dip cast on stainless steel mandrels, dried and water extracted from a 8% solids solution of the copolymer in dimethylformamide prepared as described in Example 2.

Hollow fibers were fabricated from the polymer solutions by dipping clean, dry 1 mm diameter stainless steel mandrels into the polymer solution. The mandrels were suspended in a baffled chamber maintained at 37° C. in a Class 1000 Cleanroom. The mandrel was attached to a motor driven cable and dipped into the polymer solution and withdrawn at an even speed. Time was allowed for the solvent to evaporate. The mandrel was inverted, hung and dipped again. This procedure was repeated three times to yield a tube with a single wall thickness of 0.75 mil. Multiple dippings were performed to reduce the chances of pinholes in the polymer hollow fibers. The mandrels were left in the heated chamber for at least 16 hours to allow the solvent to evaporate. To aid in the removal of the hollow fibers from the mandrel, the coated mandrel was soaked in distilled water for one hour. The removal of any remaining residual solvent was achieved by water extracting the hollow fibers in distilled water for 24 hours. The hollow fibers were then flushed three times with distilled water and packaged in distilled water in clean glass tubes. Prior to filling the hollow fiber with islet cells the hollow fibers were leak tested. One end of the hollow fibers was heat-sealed, the tube was filled with distilled water and the remaining end was heat-sealed. The filled hollow fiber was pressurized and the tube was examined for water leakage.

The extracted hollow fibers were then sterilized by "liquid cycle" autoclave sterilization and stored in a sterile environment until they are used.

Example 12
Maintenance of Cell Distribution within Membrane.

Optimal diffusion of intracellular products out of a membrane implant is achieved, in part, by maintaining an even distribution of the cells within the membrane. It has been known to use hydrophilic natural polymers to encapsulate mammalian cells. Generally, mammalian cells have been microencapsulated through crosslinking using, for example, alginate and polylysine. One drawback to microencapsulation using certain crosslinked hydrophilic polymers is the tendency of crosslinked polymers to biodegrade.

It is also known that alginates and some vegetable gums are capable of forming high water content gels suitable as encapsulating agents. Gels where the water content is higher than 99.5% have been produced. The high water content of these gels provides these gels with high permeability to the various permeants important to hybrid artificial organs. Even at very high water contents, these gels are very viscous and thus capable of immobilizing cells dispersed within the gel. However, one drawback to the use of some of these acrylic hydrogels is their biodegradability, particularly when the gels are implanted as microcapsules directly into tissue.

By placing these high water content hydrogels within the membranes of the instant invention, it has been found that the hydrogel compositions do not rapidly biodegrade once implanted. Thus a preferred embodiment of the instant invention is the use of a hydrophilic gel with a water content ≧ of about 35% water but preferably ≧90% water inside of a dense, semi-permeable polymer membrane. The dense membranes of the instant invention provide immunoisolation and necessary selective permeability while also providing an absolute barrier to cells. The water swollen gel fixes the position of the cells within the dense membrane (e.g. in the shape of a hollow fiber) to prevent bunching. In addition, the high water content of the water swollen gel provides low resistance to the permeability of species leaving or arriving at the contained cells.

The dense membrane may also provide a biostable protective layer to the water-swollen gel, thus preventing or reducing biodegradation of the gel.

Suitable dense membranes include but are not limited to hydrophilic or amphipathic polyurethanes having ≧ about 20% water but preferably ≧50% water but less equilibrium water content than the water-swollen gel. Water content is measured in water @ 37° C. and expressed as a percentage of the wet weight of the sample after maximum weight gain has occurred. This value is determined by weighing the polymer wet and again after the polymer has been dried to equilibration at standard laboratory conditions, e.g. ~23° C. and 50% relative humidity.

Suitable hydrogels are alginates (e.g. sodium alginate, ammonia alginates, potassium alginates, propylene glycol alginates, algins), guar gum, gum tragacanth, locust bean gum, methocel, xanthan gum, polyethylene oxide, polypropylene oxide, dextrans, acrylates, methacrylates, polyvinyl alcohol, polyvinyl pyrolidone and combinations of the above.

Those gums or resins capable of "crosslinking" may be used crosslinked or linear. For example, sodium alginate may be used "as is" or converted to its insoluble calcium form.

The most preferred hydrogel is calcium alginate wherein the water content is greater than about 90%.

With regard to all of the above-described devices, it is preferred that the devices further comprise a hydrogel, that comprises greater than about 35% water, within the cavity of the device. The hydrogel serves to immobilize the cells within the device, thus insuring an even cell distribution within the device.

The most preferred embodiment of the instant invention comprises the implantation of a dense membrane in the form of hollow fibers where the hollow fiber is filled with calcium alginate with a water content greater than about 90%. However, it is understood that the geometry of the dense membrane can be in any form including sheets, larger diameter tubes, etc.

A further description of the preparation and use of hydrogels is provided by co-file, co-pending U.S. Patent Application entitle METHOD OF CULTURING VIABLE CELLS AND METHOD OF REGULATING BLOOD GLUCOSE LEVELS BY IMPLANTATION OF VIABLE CELLS IN NON-POROUS, SEMI-PERMEABLE POLYMERIC MEMBRANES by Robert S. Ward, John Monahan and Robert Kuhn (Attorney Docket No. SOMA-20111, the text of which relating to the use of hydrogels is incorporated herein by reference.

Example 13

Measurement of Permeability and Mathematical Model

The most widely used method for comparing polymers according to their moisture vapor transmission rates (MVTR) is the ASTM E96 method. The results are most often expressed as grams of water transmitted per day per square meter of film area, rather than in typical units of p, referred to above. The driving force associated with the permeation of a substance is determined by the conditions of the experiment, but is not always reported in convenient units. In order for the data to be meaningful, these factors must be taken into consideration as well as reporting the data in reference to the thickness of the membrane. The normalization to a unit thickness, such as mils, may be done by multiplying the MVTR by the film thickness in the same units.

Two variations of the ASTM E96-80 method are presently popular. The first, called the Upright-Cup method, is known as E-96–80 Procedure B. In this procedure, standard cups are filled with water to a prescribed depth and sealed with the sample. The cups are accurately weighed and placed upright in an environment maintained at 23° C. and 50% relative humidity (RH) with an air velocity of 500 to 600 ft/minute parallel to the sample. The sample is in contact with the vapor space within the cup, which is also at 23° C. and 100% RH. Following a transient time lag period at the beginning of the experiment, weight loss versus time at steady state is measured and used to calculate MVTR from the area of the sample. The vapor pressure driving force ($\Delta$V.P.) in the ASTM E-96 Procedure B is a constant 10.5 mm Hg.

The other is the Inverted-Cup method, Procedure BW. The conditions for this procedure are in general similar to those used in the upright cup method, except that the cup is inverted so that water contacts the sample.

At the present time, there are few published tabulations of polymer MVTR values available. One mil film values may be calculated from their published water vapor permeability constants as described above. The MVTR value, as determined by the Upright Cup method, may vary over nearly four orders of magnitude, from $<0.1$ for polyvinylidenechloride to $>800$ g/$M^2$/day for the present hydrophilic polyurethanes. Although part of the variation is due to the varying levels of crystallinity within the range of polymers cited, the wide range of values illustrates that very significant changes in permeability may be obtained through changes in membrane chemistry.

Using the computer software program MATHEMATICA ®, for doing mathematical calculations, the inventors developed an analytical model for the non-steady-state diffusion of solutes in a closed diffusion cell, which is well suited for conducting protein permeability studies utilizing two-chamber dialysis/diffusion cells. The use of these simple cells allows several experiments to proceed in parallel due to the small size and simplicity of the apparatus. The membranes are hydrated and the diffusion cells are assembled and leak-tested, then completely filled with, e.g., solute-free phosphate-buffered saline (PBS) in one chamber, chamber 2, and solute-containing PBS in a second chamber, chamber 1. No air interface is allowed between the two chambers. To avoid concentration polarization, the cells may be placed on a gentle mechanical shaker, e.g., in an incubator with temperature control for maintaining the temperature at, e.g., 37° C. The permeant concentration in chamber 2 may be measured by sensitive calorimetric methods using a visible light spectrophotometer and appropriate reagent kits. (Bradforn, M. M., "A Refined and Sensitive Method for the Quantitation of Microgram Quantities of Protein Utilizing the Principle of Protein-Dye Binding", Anal Biochem, 72:248 (1976); Sedmark, J. J. and Grossberg, S. E., "A Rapid, Sensitive and Versatile Assay for Protein Using Commassie Brillant Blue G250, Anal Biochem, 79:544 (1977), Keilin D. and Hartree EF, "Properties of Glucose Oxidase [notatin]", Biochem J 42:221, (1948), and Keilin D. and Hartree EF, "Specificity of glucose oxidase[notatin]. Biochem J 50:331, (1952)).

Side 1, the side of the membrane facing chamber 1, is charged with a permeant solution with 0.03% sodium azide to retard bacterial contamination in solution at concentration, $c_{1o}$, and the concentration of the solution is monitored on side two, $c_2$, as a function of time, t, while controlling temperature and agitation to determine the permeability coefficient, p, of the membrane. It is also of interest to determine the time, t, at which concentration, $c_2$, will reach a specific value under conditions of known p, $c_{1o}$, $c_{2o}$, a, $v_1$, $v_2$, and l.

According to Fick's Law, the flux of permeant through a membrane is proportional to the concentration driving force across the membrane, $c_1-c_2$, and the membrane area, a, and inversely proportional to the membrane thickness, l. The permeability coefficient, p, is the proportionality constant linking the solubility and diffusivity coefficients and the liquid film resistance together.

In this model it is assumed that p is independent of the driving force in the water-swollen membrane. It is also assumed that the flux is proportional to the area and inversely proportional to the thickness.

At equilibrium, the net flux across the membrane stops. If $v1=v2$, equilibrium will be reached at $$c1=c2=clo/2$$

For unequal cell compartment volumes, i.e., $v1 \neq v2$, the equilibrium may be calculated as if $v1$ at $clo$ and $v2$ at $c2o$ were simply mixed together, i.e., $$ceq = (clo\ v1 + c2o\ v2)/(v1+v2),$$

wherein ceq is the equilibrium concentration in both chambers.

The driving force in membrane permeation is the difference between the upstream concentration, c1, and the downstream concentration, c2, of the permeant. The quantity (c1-c2) changes continuously during the course of a non-steady-state experiment. After an initial transient period, only a single chamber-2 concentration measurement is needed to calculate the permeability constant p according to the following equations.

| | |
|---|---|
| $t = 0, c1 = clo$ and $c2 = c2o$ | Known Initial Conditions |
| $t = \infty,$ | Equilibrium |
| $c1 = c2 = ceq = (clo\ v1 + c2o\ v2)/(v1+v2)$ | |
| $t = t, c1v1 + c2v2 = clov1 + c2ov2$ | Conservation of Mass | wherein
- $clo$ = initial permeant concentration in chamber 1 (g/cc),
- $v1$ = volume of chamber 1 (cc),
- $c2o$ = initial permeant concentration in chamber 2 (g/cc),
- $v2$ = volume of chamber 2 (cc),
- $a$ = membrane area (cm$^2$)',
- $l$ = membrane thickness (cm),
- $t$ = time (days), and
- $p$ = permeability coefficient (ugcm/daycm$^2$g/mL).

Thus, $$p = -\left( \frac{l\ v1\ v2\ \text{Log}\left[ \frac{-c2 + (clo\ v1 - c2v2)/v1}{clo - c2o} \right]}{a\ t(v1 + v2)} \right) \cdot 10^6$$

If an experiment is performed in a diffusion cell with equal chamber volumes, i.e., $v1 = v2 = v$, and $c2o$ is equal to zero, the equation is reduced to the following equation.

$$p = -(lv\ \text{Log}\ [1-((2\ c2/clo)]/(2\ a\ t))*10^6$$

The invention now being fully described, it will be apparent to one of ordinary skill in the art that many changes and modifications can be made thereto without departing from the spirit or scope of the invention as set forth herein.

We claim:

1. A biocompatible, hydrophilic, segmented block polyurethane copolymer having a number average molecular weight of about 5,000 to 150,000,
   comprising about 5 to 45 wt % of at least one hard segment; and
   about 95 to 55 wt % of at least one soft segments comprising at least one hydrophilic, hydrophobic or amphipatic oligomer selected from the group consisting of aliphatic polyols, aliphatic and aromatic polyamines and mixtures thereof; the copolymer being capable of forming a substantially nonporous semi-permeable film having a tensile strength greater than about 350 psi and up to about 10,000 psi, an ultimate elongation greater than about 300% and up to about 1,500 t and a water absorption such that the sum of the volume fraction of absorbed water and the hydrophilic volume fraction of the soft segment exceeds about 100% and up to about 2,000% of the dry polymer volume and exceeds about 50% and up to about 95% of the wet polymer volume and being permeable to monodisperse molecules of up to about 6,000 to 600,000 molecular weight and substantially impermeable to particulate matter.

2. The copolymer of claim 1, wherein the volume fraction of absorbed water is about 50% or greater than the total volume of the water swollen polymer.

3. The copolymer of claim 1, wherein the aliphatic polyols of the soft segment are selected from the group consisting of linear, branched and graft polyarylene, polyalylene and polyalkenyline oxides, random and block copolymers thereof, polycarbonate polyols, hydroxyl-terminated silicones, random and block copolymers thereof with polyalkylene oxides, linear and branched polyalkenyl, and polyalkylene polyols, and mixtures thereof.

4. The copolymer of claim 1, wherein the soft segment is selected from the group consisting of amine-terminated polyalkylene oxides and random, block and graft copolymers thereof, amine-terminated polydialkylsiloxanes, random and block copolymers thereof with polyalkylene oxides and mixtures thereof.

5. The copolymer of claim 1, further comprising an end group selected from the group consisting of monofunctional aliphatic polyols, aliphatic or aromatic amines and mixtures thereof.

6. The copolymer of claim 5, wherein
   (a) the monofunctional aliphatic polyols of the end group are selected from the group consisting of monofunctional polyalkylene oxides, siloxanes and mixtures thereof; and
   (b) the monofunctional amines of the end group are selected from the group consisting of dialkylamines, amine functionalized siloxanes, amine terminated polyakylene oxides and mixtures thereof.

7. The copolymer of claim 1, wherein the soft segment is selected from the group consisting of reaction products of an organic diisocyanate with a polyamine and a polyol.

8. The copolymer of claim 7, wherein the organic diisocyanate of the hard segment is selected from the group consisting of alkyl diisocyanates, arylalkyldiisocyanates, alkyl-cycloalkyl diisocyanates, alkylaryl diisocyanates, cycloalkyl diisocyanates, aryl diisocyanates, and cycloalkylaryl diisocyanates, which may be further substituted with oxygen, and mixtures thereof.

9. The copolymer of claim 7, wherein the polyol of the hard segment is selected from the group consisting of alkylene, cycloalkylene and arylene diols, triols, tetraalcohols, pentaalcohols and mixtures thereof.

10. The copolymer of claim 7, wherein the polyamine of the hard segment is selected from the group consisting of alkyl, cycloalkyl, and aryl amines, which may be further substituted with N, O or halogen, complexes thereof with alkali metal salts, and mixtures thereof.

11. The copolymer of claim 1, wherein the soft segment comprises a polyethyleneoxide of molecular weight greater than about 3,000 daltons.

12. The copolymer of claim 11, wherein the polyethyleneoxide has a molecular weight of about 8,000 or greater.

13. The copolymer of claim 6, wherein the soft segment comprises a blend of polyols selected from the group consisting of a polyethyleneoxide of molecular weight greater than about 3,000 daltons, a polyethyleneoxide-polytetramethyleneoxide copolymer and a polyethyleneoxide homopolymer, a polyethyleneoxide-polytetramethyleneoxide copolymer and an ethyleneoxide-capped polyethyleneoxide copolymer, a polyethyleneoxide-polypropyleneoxide copolymer and a polyethyleneoxide homopolymer, a polyethyleneoxide-polypropyleneoxide copolymer and a polypropyleneoxide homopolymer, a polyethyleneoxide homoploymer and a polytetramethyleneoxide homopolymer, a polyethyleneoxide copolymer and a polycarbonate homopolymer, a polyethyleneoxide copolymer and a polybutadiene homolymer, and a polyethyleneoxide copolymer and a polyisobutylene homopolymer.

14. The copolymer of claim 13, wherein the soft segment comprises a blend of a polyethyleneoxide-polytetramethyleneoxide copolymer and polyethyleneoxide homopolymer.

15. The copolymer of claim 13, wherein the soft segment is a blend of a polyethyleneoxide-polytetramethyleneoxide copolymer and a polyethyleneoxide-polypropyleneoxide copolymer.

16. The copolymer of claim 13, wherein the soft segment is a blend of a polyethyleneoxide-polytetramethyleneoxide copolymer and an ethyleneoxide-capped polypropyleneoxide polymer.

17. The copolymer of claim 13, wherein the soft segment is a blend of a polyethyleneoxide-polypropyleneoxide copolymer and a polyethyleneoxide homopolymer.

18. The copolymer of claim 13, wherein the soft segment is a blend of a polyethyleneoxide-polypropyleneoxide copolymer and a polypropyleneoxide homopolymer.

19. The copolymer of claim 13, wherein the soft segment is a blend of a polyethyleneoxide homopolymer and a polytetramethyleneoxide homopolymer providing the copolymer having a lesser tensile strength and elongation in the wet state than in its dry state.

20. The copolymer of claim 13, wherein the soft segment is a blend of a polyethyleneoxide-containing copolymer and a polycarbonate homopolymer.

21. The copolymer of claim 13, wherein the soft segment is a blend of a polyethyleneoxide-containing copolymer and a polybutadiene homopolymer.

22. The copolymer of claim 13, wherein the soft segment is a blend of a polyethyleneoxide-containing copolymer and a polyisobutylene homopolymer.

23. A non-porous, semi-permeable, biocompatible film formed from the block copolymer of claim 1.

24. The non-porous film of claim 23, in the form of a flexible sheet or a hollow membrane.

25. The non-porous film of claim 23, being attached to a substrate.

26. The non-porous film of claim 25, in the form of a coating deposited onto a substrate.

27. The non-porous film of claim 26, wherein the substrate is a woven or knitted substrate or a porous polymer.

28. The non-porous film of claim 25, having a thickness of about 1 to 150 microns.

29. The non-porous film of claim 23, having a thickness of about 5 to 150 microns.

30. A method of permeating molecules of a predetermined molecular weight range while substantially preventing the passage of cells and particulate matter between two fluids comprising interposing between the two fluids the nonporous film of claim 23.

31. A biocompatible, hydrophilic, segmented or block polyurethane copolymer having a number average molecular weight of about 5,000 to 150,000, comprising
   about 5 to 45% of at least one hard segment selected from the group consisting of reaction products of an organic diisocyanate and a polyamine and a polyol; and
   about 95 to 55 wt % of a hydrophilic soft segment comprising a blend of a polyethyleneoxide-polytetramethyleneoxide copolymer and a polyethyleneoxide homopolymer.

32. The block polyurethane copolymer of claim 31, wherein the organic dissocyanate comprises 4,4'-diphenylmethane diisocyanate.

33. The block polyurethane copolymer of claim 31, wherein the organic diisocyanate comprises hydrogenated diphenylmethane diisocyante.

34. The block polyurethane copolymer of claim 31, wherein the hard segment polyol comprises an alkylenediol.

35. The block polyurethane copolymer of claim 34, wherein the hard segment polyol comprises butanediol.

36. The block polyurethane copolymer of claim 31, wherein the hard segment polyamine comprises an alkylenediamine.

37. The block polyurethane copolymer of claim 36, wherein the hard segment polyamine comprises ethylenediamine.

38. A non-porous film made from the polymer of claim 31.

39. The film of claim 31, being attached to a substrate.

40. A biocompatible, hydrophilic, segmented or block polyurethane copolymer having a number average molecular weight of about 5,000 to 150,000, comprising
   about 5 to 45 wt % of a least one hard segment selected from the group consisting of reaction products of an organic diisocyanate and a polyamine and a polyol; and
   about 95 to 55 wt % of a hydrophilic soft segment comprising a blend of polyethyleneoxide-polytetramethyleneoxide copolymer and a polyethyleneoxide-polypropylene oxide copolymer.

41. The block polyurethane copolymer of claim 40, wherein the organic diiisocyanate comprises 4,4'-diphenylmethane diisocyanate (MDI).

42. The block polyurethane copolymer of claim 40, wherein the organic diisocyanate comprises hydrogenated diphenylmethane diisocyanate (HMDI).

43. The block polyurethane copolymer of claim 40, wherein the hard segment polyol comprises an alkylenediol.

44. The block polyurethane copolymer of claim 43, wherein the hard segment polyol comprises butanediol.

45. The block polyurethane copolymer of claim 40, wherein the hard segment polyamine comprises an alkylenediamine.

46. The block polyurethane copolymer of claim 40, wherein
the hard segment polyamine is ethylene diamine.

47. A non-porous film made from the polymer of claim 40.

48. The non-porous film of claim 47, being attached to a substrate.

49. A biocompatible, hydrophilic, segmented or block polyurethane copolymer having a number average molecular weight of about 5,000 to 150,000, comprising
about 5 to 45 wt % of at least one hard segment selected from the group consisting of reaction products of an organic diisocyanate and a polyamine and a polyol; and
about 95 to 55 wt % of a soft segment comprising a blend of a polyethyleneoxide-homopolymer and a polyethyleneoxide-polypropylene oxide copolymer.

50. The block polyurethane copolymer of claim 49, wherein the organic diisocyanate comprises 4,4'-diphenylmethane diisocyanate (MDI).

51. The block polyurethane copolymer of claim 49, wherein the organic diisocyanate comprises hydrogenated diphenylmethane diisocyanate (HMDI).

52. The block polyurethane copolymer of claim 49, wherein the hard segment polyol comprises an alkylenediol.

53. The block polyurethane copolymer of claim 52, wherein the hard segment polyol comprises butanediol.

54. The block polyurethane copolymer of claim 49, wherein the hard segment polyamine comprises an alkylenediamine.

55. The block polyurethane copolymer of claim 54, wherein the hard segment polyamine comprises ethylenediamine.

56. A nonporous film, made from the polymer of claim 49.

57. The non-porous film of claim 56, being attached to a substrate.

* * * * *